US012667456B2

(12) United States Patent
Zenz-Olson et al.

(10) Patent No.: US 12,667,456 B2
(45) Date of Patent: Jun. 30, 2026

(54) TENSIONABLE AND LOCKABLE MICRO SUTURE ANCHORS AND ANCHOR ARRAYS FOR ANATOMICAL ATTACHMENT OF SOFT TISSUE TO BONE

(71) Applicant: Integrity Orthopaedics, Inc., Orono, MN (US)

(72) Inventors: Zak Zenz-Olson, Ham Lake, MN (US); Nathaniel Van Tran, Lakeville, MN (US); Thomas A. Westling, Orono, MN (US); Howard W. Harris, Southlake, TX (US); Marc Labbé, Spring, TX (US); Patrick M. Connor, Charlotte, NC (US)

(73) Assignee: Integrity Orthopaedics, Inc., Maple Plain, MN (US)

( * ) Notice: Subject to any disclaimer, the term of this patent is extended or adjusted under 35 U.S.C. 154(b) by 140 days.

(21) Appl. No.: 17/679,880

(22) Filed: Feb. 24, 2022

(65) Prior Publication Data

US 2022/0323198 A1      Oct. 13, 2022

Related U.S. Application Data

(60) Provisional application No. 63/281,411, filed on Nov. 19, 2021, provisional application No. 63/231,136, (Continued)

(51) Int. Cl.
*A61F 2/08* (2006.01)
*A61B 17/04* (2006.01)

(52) U.S. Cl.
CPC ..... *A61F 2/0811* (2013.01); *A61B 2017/0409* (2013.01); *A61B 2017/0417* (2013.01);
(Continued)

(58) Field of Classification Search
CPC ............ A61F 2/0811; A61F 2002/0882; A61F 2002/30461; A61F 2220/0075;
(Continued)

(56) References Cited

U.S. PATENT DOCUMENTS 4,899,743 A     2/1990  Nicholson et al.
4,968,315 A    11/1990  Gatturna
(Continued)

*Primary Examiner* — Sarah W Aleman
*Assistant Examiner* — Rebecca Lynee Zimmerman
(74) *Attorney, Agent, or Firm* — Seager, Tufte & Wickhem LLP

(57) ABSTRACT

A toggle-type suture anchor that incorporates individual suture tensioning and locking without knot tying. The anchor includes several exemplary designs of toggle bodies having a working suture pre-threaded through one or more passages therethrough. A locking suture loop is pre-threaded relative to the working suture and includes a collapsible loop that encircles a portion of the length of suture running longitudinally adjacent the side of the anchor. With the loop open, the working suture can slide through the anchor, however, when the loop is closed the working suture is locked in position to retain tension on the working suture. Alternatively, the locking suture loop can be replaced with a mechanical locking member that moves from a first unlocked to a second locked position. The exemplary anchors can be utilized in a pre-strung connected array of anchors.

20 Claims, 29 Drawing Sheets

Related U.S. Application Data filed on Aug. 9, 2021, provisional application No. 63/172,565, filed on Apr. 8, 2021.

(52) U.S. Cl.
CPC ................. *A61F 2002/0817* (2013.01); *A61F 2002/0852* (2013.01); *A61F 2002/0882* (2013.01); *A61F 2250/0012* (2013.01)

(58) Field of Classification Search
CPC ...... A61F 2002/0817; A61F 2002/0852; A61F 2250/0012; A61F 2002/0888; A61B 17/04; A61B 17/0401; A61B 2017/0404; A61B 2017/0406; A61B 2017/0414; A61B 2017/0446; A61B 2017/0459; A61B 2017/0462; A61B 2017/0403–0464; A61B 2017/0409; A61B 2017/0475; A61B 2017/0417; A61B 2017/0448; A61B 2017/045; A61B 2017/06052; A61B 2017/927
See application file for complete search history.

(56) References Cited

U.S. PATENT DOCUMENTS

| | | | |
|---|---|---|---|
| 5,041,129 A | 8/1991 | Hayhurst et al. | |
| 5,192,303 A | 3/1993 | Gatturna et al. | |
| 5,203,787 A | 4/1993 | Noblitt et al. | |
| 5,207,679 A | 5/1993 | Li | |
| 5,269,809 A | 12/1993 | Hayhurst et al. | |
| 5,403,348 A | 4/1995 | Bonutti | |
| 5,405,359 A | 4/1995 | Pierce | |
| 5,468,197 A | 11/1995 | Loeffler | |
| 5,584,835 A | 12/1996 | Greenfield | |
| 5,626,614 A | 5/1997 | Hart | |
| 5,669,935 A | 9/1997 | Rosenman et al. | |
| 5,683,418 A | 11/1997 | Luscombe et al. | |
| 5,725,557 A | 3/1998 | Gatturna et al. | |
| 5,728,100 A | 3/1998 | Skiba | |
| 5,741,300 A | 4/1998 | Li | |
| 5,810,848 A | 9/1998 | Hayhurst | |
| 5,891,168 A | 4/1999 | Thal | |
| 5,921,986 A | 7/1999 | Bonutti | |
| 5,948,002 A | 9/1999 | Bonutti | |
| 5,961,538 A | 10/1999 | Pedlick et al. | |
| 6,056,773 A | 5/2000 | Bonutti | |
| 6,066,160 A | 5/2000 | Colvin et al. | |
| 6,117,161 A | 9/2000 | Li et al. | |
| 6,270,518 B1 | 8/2001 | Pedlick et al. | |
| 6,293,961 B2 | 9/2001 | Schwartz et al. | |
| 6,451,030 B2 | 9/2002 | Li et al. | |
| 6,500,195 B2 | 12/2002 | Bonutti | |
| 6,520,980 B1 | 2/2003 | Foerster | |
| 6,527,795 B1 | 3/2003 | Lizardi | |
| 6,547,800 B2 | 4/2003 | Foerster et al. | |
| 6,592,609 B1 | 7/2003 | Bonutti | |
| 6,645,227 B2 | 11/2003 | Fallin et al. | |
| 6,660,023 B2 | 12/2003 | McDevitt et al. | |
| 6,726,707 B2 | 4/2004 | Pedlick et al. | |
| 6,773,436 B2 | 8/2004 | Donnelly et al. | |
| 6,843,799 B2 | 1/2005 | Bartlett | |
| 6,972,027 B2 | 12/2005 | Fallin et al. | |
| 6,986,781 B2 | 1/2006 | Smith | |
| 7,041,120 B2 | 5/2006 | Li et al. | |
| 7,081,126 B2 | 7/2006 | McDevitt et al. | |
| 7,232,455 B2 | 6/2007 | Pedlick et al. | |
| 7,320,701 B2 | 1/2008 | Haut et al. | |
| 7,556,640 B2 | 7/2009 | Foerster | |
| 7,566,339 B2 | 7/2009 | Fallin et al. | |
| 7,641,672 B2 | 1/2010 | Fallin et al. | |
| 7,645,293 B2 | 1/2010 | Martinek et al. | |
| 7,674,275 B2 | 3/2010 | Martin et al. | |
| 7,682,374 B2 | 3/2010 | Foerster et al. | |
| 7,722,644 B2 | 5/2010 | Fallin et al. | |
| 7,806,909 B2 | 10/2010 | Fallin et al. | |
| 7,875,064 B2 | 1/2011 | Donnelly et al. | |
| 7,909,851 B2 | 3/2011 | Stone et al. | |
| 7,963,972 B2 | 6/2011 | Foerster et al. | |
| 8,052,719 B2 | 11/2011 | Paulos | |
| 8,118,835 B2 | 2/2012 | Weisel et al. | |
| 8,298,262 B2 | 10/2012 | Stone et al. | |
| 8,348,975 B2 | 1/2013 | Dreyfuss | |
| 8,366,744 B2 | 2/2013 | Bojarski et al. | |
| 8,419,794 B2 | 4/2013 | ElAttrache et al. | |
| 8,425,536 B2 | 4/2013 | Foerster et al. | |
| 8,449,584 B2 | 5/2013 | Donnelly et al. | |
| 8,454,655 B2 | 6/2013 | Yeung et al. | |
| 8,512,375 B2 | 8/2013 | Torrie et al. | |
| 8,771,314 B2 | 7/2014 | Crombie et al. | |
| 8,777,992 B2 | 7/2014 | Yeung et al. | |
| 8,828,052 B2 | 9/2014 | Caborn et al. | |
| 8,845,699 B2 | 9/2014 | Bonutti | |
| 8,932,331 B2 | 1/2015 | Kaiser et al. | |
| 8,951,287 B1 | 2/2015 | Green et al. | |
| 8,986,346 B2 | 3/2015 | Dreyfuss | |
| 9,072,509 B2 | 7/2015 | Stoll, Jr. et al. | |
| 9,173,651 B2 | 11/2015 | Stone et al. | |
| 9,192,369 B2 | 11/2015 | Bittenson | |
| 9,216,036 B2 | 12/2015 | Johnstone | |
| 9,220,493 B2 | 12/2015 | Hart et al. | |
| 9,265,495 B2 | 2/2016 | Petersen et al. | |
| 9,271,714 B2 | 3/2016 | Martin | |
| 9,301,756 B2 | 4/2016 | Wardle | |
| 9,307,979 B1 | 4/2016 | Bennett et al. | |
| 9,314,238 B2 | 4/2016 | Martin | |
| 9,345,467 B2 | 5/2016 | Lunn et al. | |
| 9,451,945 B2 | 9/2016 | Hawkins | |
| 9,463,008 B2 * | 10/2016 | Thal ................... A61B 17/0401 |
| 9,504,462 B2 | 11/2016 | Dooney, Jr. et al. | |
| 9,526,489 B2 | 12/2016 | Burkhart | |
| 9,532,777 B2 | 1/2017 | Kaiser et al. | |
| 9,539,000 B2 | 1/2017 | Hendricksen et al. | |
| 9,545,251 B2 | 1/2017 | Bojarski et al. | |
| 9,597,070 B2 | 3/2017 | Bittenson | |
| 9,655,611 B2 | 5/2017 | Green et al. | |
| 9,693,765 B2 | 7/2017 | Sullivan et al. | |
| 9,713,463 B2 | 7/2017 | Oren et al. | |
| 9,763,719 B2 | 9/2017 | Snyder et al. | |
| 9,814,565 B2 | 11/2017 | Foerster et al. | |
| 9,872,678 B2 | 1/2018 | Spenciner et al. | |
| 9,931,150 B2 | 4/2018 | Philippon et al. | |
| 10,130,354 B2 | 11/2018 | Dooney, Jr. | |
| 10,172,607 B2 | 1/2019 | Burkhart | |
| 10,178,989 B2 | 1/2019 | Bennett et al. | |
| 10,285,684 B2 | 5/2019 | Spenciner et al. | |
| 10,368,856 B2 | 8/2019 | Stone et al. | |
| 10,376,260 B2 | 8/2019 | Bojarski et al. | |
| 10,398,428 B2 | 9/2019 | Denham et al. | |
| 10,478,172 B1 | 11/2019 | Williams et al. | |
| 10,543,075 B2 | 1/2020 | Gregoire et al. | |
| 10,575,842 B2 | 3/2020 | Lund | |
| 10,588,614 B2 | 3/2020 | Gittings et al. | |
| 10,603,029 B2 | 3/2020 | Kaiser et al. | |
| 10,667,803 B2 | 6/2020 | Lizardi | |
| 10,675,015 B2 | 6/2020 | Guo et al. | |
| 10,729,421 B2 | 8/2020 | Stone et al. | |
| 10,772,622 B2 | 9/2020 | Santangelo et al. | |
| 10,786,235 B2 | 9/2020 | Sorensen et al. | |
| 10,863,979 B2 | 12/2020 | Sorensen et al. | |
| 10,952,719 B2 | 3/2021 | Lombardo et al. | |
| 10,966,704 B2 | 4/2021 | Lozier et al. | |
| 10,987,099 B2 | 4/2021 | Stone et al. | |
| 2006/0178702 A1 | 8/2006 | Pierce et al. | |
| 2007/0083236 A1 * | 4/2007 | Sikora ................ A61B 17/0401 |
| | | | 606/232 |
| 2009/0312782 A1 | 12/2009 | Park | |
| 2011/0022061 A1 * | 1/2011 | Orphanos .......... A61B 17/0469 |
| | | | 606/232 |
| 2011/0288584 A1 * | 11/2011 | Bojarski ............ A61B 17/0401 |
| | | | 606/232 |
| 2013/0158598 A1 * | 6/2013 | Lizardi .............. A61B 17/0401 |
| | | | 606/232 |
| 2013/0190815 A1 | 7/2013 | Mansmann | |

(56)     References Cited

U.S. PATENT DOCUMENTS

| 2015/0250470 | A1 |  | 9/2015 | Vargas |
| 2017/0100183 | A1 | * | 4/2017 | Iaizzo ................ A61B 18/1492 |
| 2020/0253715 | A1 |  | 8/2020 | Trenhaile |
| 2020/0315775 | A1 |  | 10/2020 | Pilgeram et al. |

* cited by examiner

263

TENSIONABLE AND LOCKABLE MICRO SUTURE ANCHORS AND ANCHOR ARRAYS FOR ANATOMICAL ATTACHMENT OF SOFT TISSUE TO BONE

CROSS REFERENCE TO RELATED APPLICATIONS

The present application claims the benefit of and priority to U.S. Prov. Pat. App. No. 63/231,136, filed Aug. 9, 2021, titled TENSIONABLE AND LOCKABLE MICRO SUTURE ANCHORS AND ANCHOR ARRAYS FOR ANATOMICAL ATTACHMENT OF SOFT TISSUE TO BONE, U.S. Prov. Pat. App. No. 63/172,565, filed Apr. 8, 2021, titled TENSIONABLE AND LOCKABLE MICRO SUTURE ANCHORS AND ANCHOR ARRAYS FOR ANATOMICAL ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosures of which are incorporated herein by reference.

BACKGROUND

Throughout the human body there are many attachments of soft tissue, such as tendons and ligaments, to bone as integral elements of motion in functioning joints such as the shoulder. The shoulder joint includes the humeral head of the upper arm bone in contact with the indentation of the glenoid working in conjunction with the rotator cuff, which is a combination of muscles and tendons forming a capsule that both stabilizes the joint and causes desired motion. Injury to the connection between tendons of the rotator cuff muscles to the humeral head, usually a tear in a tendon, is common. These tears do not self-heal. It is estimated that in the U.S. over 4 million people annually are referred to a surgeon due to shoulder pain and over 500,000 of these referrals result in shoulder surgery to repair the rotator cuff.

Significant effort has been expended over the past 30 years to develop bone and tissue anchor devices and methods to respond to the need for effective rotator cuff repair. Early methods and devices utilized an open surgical technique that required a large incision of 4 to 6 cm and cutting the deltoid muscle, then re-attaching after the rotator cuff repair. This method is still used today for massive tears by some surgeons due to high success rate, however, the procedure is associated with deltoid dysfunction, significant pain during recovery and extensive rehabilitation time. Due to the invasiveness of the open surgery and resulting rehabilitation time, a "mini-open" procedure and associated devices were developed in the early 1990's, wherein the surgeon uses partial arthroscopic techniques followed by an incision and split of the deltoid muscle fibers to access the rotator cuff tendon for repair. By the late 1990's, devices and instruments were further developed to complete the repair of rotator cuff tendon attachment to bone using all-arthroscopic techniques, with further resultant reduction in trauma and recovery time.

Arthroscopic repair of the rotator cuff tendon attachments to the humeral head are the most common technique used today. However, it is recognized that these all-arthroscopic techniques are quite difficult to perform and achieve varying results. The skill of the surgeon with the technology available is a known factor related to the procedure's success. Even with the last 20 years of all-arthroscopic technologic advancement and experience, deficiencies persist as evidenced by studies indicating an overall average rotator cuff repair failure rate of 20% to 40%, with a highly variable range of 4% to 90% in individual studies. The study results indicate failure rates are much higher for large or massive tendon tears and there are vast variations in failure rates between surgeons, as well as with respect to various patient factors, equipment used, and type of repair completed.

There is significant controversy among professionals as to the reasons for the high incidence of arthroscopic rotator cuff repair failure (i.e. "re-tear of the rotator cuff"). However, studies clearly show there is a need to reduce the failure rate of arthroscopic rotator cuff repair to avoid its effects of patients' lack of mobility, functional deficits, increased pain and/or requiring subsequent and more invasive surgery with the attendant pain and rehabilitation. In particular, there is great concern for patients who have some degree of native tendon or repaired tendon failure yet choose to "live with it" rather than going through a first or another surgery and rehabilitation, thus affecting quality of life and promoting continued joint degradation from lack of use.

The basic device or devices used for repair of a tendon torn from a bone is one or more suture anchors in which a mechanical structure provides an anchor to the bone and a suture or sutures extend therefrom for attachment to the soft tissue or tendon. Many types of anchor technologies have been proposed and used in procedures. A review of the prior art patent literature indicates over a thousand designs for suture anchors, bone anchors, tendon repair systems, delivery devices and methods espousing improved features over the past 25 years, yet repair failure rate is still unacceptable indicating the need for further improvement in the area of arthroscopic reattachment of tendons to bone and in particular in rotator cuff repair.

Overview

The present inventors have recognized, among other things, that a problem to be solved is the need for new and/or alternative devices and methods for arthroscopically affixing a tendon or other soft tissue to bone, such as in rotator cuff repair, with low failure rate, preferably under 10% on average, with little variation between surgeons, patient characteristics, and the system/method used for repair. The disclosed devices, systems, and methods, along with a statement of the problem being solved by each element are included in summary form followed by a description of specific claimed structure or methods in the present disclosure.

The present disclosure includes a total system for re-attaching a tendon that has at least in part torn away from a bone attachment or footprint. The system is useful in repair of a rotator cuff tendon that has torn away from a bone but can be used in other soft tissue and tendon repair procedures. The system is particularly useful in repair of the rotator cuff by reattaching a torn tendon, such as the most-commonly-torn supraspinatus tendon, to the humeral head of the arm. In larger tears, the infraspinatus tendon may also be torn and amenable to repair with this system. The repair is an anatomical repair, meaning that the system, devices and methods result in a repaired tendon and bone combination that closely approximates the prior natural, anatomic relationship between that tendon and bone to promote healing and provide pain-free full function to the healed repair. An anatomical repair using the presently described system may also seal the tendon in position, taking advantage of local synovial fluid to aid healing and improve post-surgery function. The system may also be used to reinforce partial tears and to secure areas beyond the region of a full-thickness tear as needed. Further, the system, as implanted can dramatically reduce recovery and rehabilitation time due to the robust nature of the repair immediately following surgery, requiring less time using a sling to limit mobility and allowing early physical therapy to maintain pre-surgery mobility and strength during healing. It is believed time in a sling and complete recovery time can be reduced at least 50%, while reducing the average failure rate to less than 10% with the current disclosed system.

As stated, in preferred examples, the exemplary rotator cuff repair is an anatomical repair in that the repaired tendon nearly duplicates or closely approximates the natural tendon and bone relationship in the fully functional joint. For example, the tendon/tendons is/are substantially and completely re-attached to the original footprint on the bone from which it was torn. The original footprint area provides the greatest likelihood of healing re-attachment of the tendon to the bone while restoring anatomy. By substantially re-attached to the original footprint it is meant that a substantial portion of the remaining torn tendon surface that was originally attached to the footprint is re-attached thereto. The current system makes possible close approximation of the original tendon attachment by allowing transtendinous or through the tendon implantation of each anchor. Thus, the tendon is held in the desired location when the anchor is installed, unlike current systems that insert anchors into exposed bone through a tear and then use suture passers (which pass the suture when the tendon is not in position) to approximate where the surgeon believes the tendon will pull down to the footprint. Further, the anatomical repair reduces micromotion at the bone to tendon interface so that healing is promoted, even during movement of the joint. Finally, access to blood for healing is improved due to utilizing substantially more small holes in the proximal humerus that are not occluded by the implant sutures to accommodate a large number of anchors in a close or high-density array.

In fresh cadaveric studies using the presently disclosed system, the repaired tendon and bone combination provides a tensile strength upon re-attachment of greater than 400 Newtons (N) and initial cyclic creep or gap formation of less than 2 millimeters (mm), preferably less than 1 mm, when cycled to a peak load on the repaired tendon per cycle of 180 N. Initial cyclic creep measures the rigidity or robustness of the attachment of the tendon to the bone as it measures how much the tendon slides or moves relative to the bone attachment. Low initial cyclic creep allows the potential for faster healing and less need for sling immobilization. Creep of less than 2 mm, or even less than 1 mm. is therefore a preferred outcome in some examples. In other words, if the tendon stays fixed in position relative to the bone it is compressed against (i.e. reduced micromotion), the healing process will occur more quickly and predictably than a situation that includes sliding of the tendon back and forth relative to the bone.

In selected embodiments, the anatomic repair requires a high-density array of knotless small anchors (requiring a bone hole size for insertion of less than 3 mm) with close spacing between anchors (less than 7 mm edge to edge, or less than 10 mm hole center to hole center) to create anchor to subsequent anchor, or serial anchor suture stitches that apply many points of constant independent force on the tendon against the bone. By independent it is meant that failure of one suture stitch to apply adequate force, as would happen if the suture stitch broke, does not affect other suture stitches. Naturally, the number of anchors utilized in a repair will depend upon the size of the tear.

It is recognized in the art that rotator cuff tears are classified into four categories based on tear size and whether a single row or double row repair is completed. Small tears are less than 1 centimeter (cm) in length; medium tears are 1 cm to 3 cm in length; large tears are 3 cm to 5 cm in length and massive tears are greater than 5 cm in length. With current devices, surgeons are limited to available large anchors and by the size of the tear as the medial anchors must fit in the tear area. For example, surgeons may use about 1 medial anchor on small tears, 1 or 2 medial anchors on medium tears and 2 or 3 medial anchors on large tears and massive tears. With the high anchor density anatomical repair of the present application, the surgeon is not limited by tear size as the anchors are implanted through the tendon and can use greater than 3 medial anchors on small tears, greater than 5 medial anchors on medium tears, and greater than 6 medial anchors on large tears and massive tears. This can include positioning implants outside the area of a full thickness tear to reinforce areas of partial thickness tears or weaker untorn tendon. Further, the present suture anchors are designed for knotless tensioning and locking to expedite implantation, maximize reproducibility amongst surgeons, and not interfere with shoulder mobility from protruding knots while eliminating the tension variations that have been found in knotted suture anchors due to the difficulty of tying knots arthroscopically.

The suture anchors of the present disclosure are bar or toggle type anchors wherein the basic structure for bone attachment is a thin elongate and/or cylindrical body having a cross sectional diameter of less than about 3 mm and a length of about 6 mm to about 10 mm. Alternative sizes could be used in other applications in the body as desired. Although described as generally cylindrical, it is recognized that certain surfaces can be machined or molded flat or grooved to allow for suture strands to run alongside the implant when placed in a circular delivery tube. That is, rather than cylindrical, the present anchors may be polygonal, for example, hexagonal or octagonal, or other cross-sectional shape. The anchor is a through the tendon or transtendinous implant as described with respect to the delivery device and method below. Being transtendinous eliminates the requirement of placing the anchors only where the tendon is absent from the bone such as in the hole formed by the tear or outside the tendon footprint. Furthermore, and importantly, the need for suture passing through the tendon is eliminated.

Transtendinous implantation with anchors used today entails technical challenges, including working a 3 mm to 6 mm diameter anchor through a hole created in the tendon with an awl, damaging the tendon. Further, threaded and flanged type anchor retention features of known, larger anchors, would damage the tendon during passing.

With a toggle type anchor, the anchor is inserted through a hole in the bone just larger than the anchor axial outer diameter. Within the bone, the anchor is toggled (aka flipped or rotated) about 90 degrees, but at least 60 degrees, so that force applied to sutures extending from the toggle body pull the length of the toggle body against the inner surface or underside of the cortical shell of the humeral head. The degree to which the toggle body rotates or moves toward the cortical shell is affected by the quality of the bone and by individual patient traits, such as age, sex, location of the hole in the bone and degree of bone degradation due to the tear. The toggle body of the current invention is designed to toggle and seat with adequate pullout strength over the range of bone qualities encountered.

The toggle body functions in conjunction with a single suture line, referred to herein as the working suture which passes through at least one passage formed through the toggle body. The number of passages can be varied in the design of the toggle body as can the way in which the working suture is threaded through the passages to provide desired tensioning and locking functions. In some embodiments the toggle body includes three holes passing through the toggle body generally perpendicular to the longitudinal axis. In this embodiment the working suture passes through the top and out the bottom of a proximal hole, then back up through the bottom of a distal hole and out the top. The working suture is flossable or slidable as positioned through the two holes by pulling with sufficient force on either working suture leg extending out the top of the toggle body. On the bottom surface of the toggle body, a length of working suture extends longitudinally past the middle hole. A suture lock, which includes a separate piece of suture or thread or other flexible cord extends through the center hole, with an adjustable or collapsible loop or slidable knot which allows the loop to be contracted, extending around the perimeter of a portion of the working suture as it passes the middle hole. The other end of the suture lock cord extends from the top of the center hole. When the top end or proximal end of the suture lock is pulled, the adjustable loop collapses tight against the working suture and can pull at least a portion of the working suture into the center hole to create a lock on the working suture so that it can no longer slide and will not slide under full load as implanted.

In alternative embodiments, the toggle can include two passages through which the working suture is threaded as described above, however, with no third passage, the locking suture described above includes a collapsible loop that surrounds the working suture as it extends from the first passage to the second passage. The bulk of the suture lock prevents sliding or flossing of the working suture through the passages in either direction.

In another alternative embodiment, the toggle body can include a single passage through which the working suture passes. A second passage can include the locking suture as described above, however, the loop of the locking suture extends around the working suture as it exits either the top or bottom of the toggle body. When tightened to a collapsed configuration around the working suture so that the working suture cannot slip through the loop, the bulk of the locking loop locks the working suture so that it can no longer floss relative the anchor in at least one direction.

The working suture can be routed through the one or more holes or passages in the toggle body in alternative patterns. For example, in addition to the paths described above, the working suture can form a one-way slip knot in which a leg of the working suture passes around the toggle body and under the other working suture leg. With this alternative embodiment, pulling on the tensioning leg of the working suture allows tensioning of the suture as it flosses through the anchor, however, tension on the second leg causes the wrapped suture leg to compress against the other suture leg to increase friction and lock the suture so that it does not floss under certain conditions.

In some embodiments, the tightening of the suture lock pulls a small portion of the working suture into a slot or channel in the bottom of the middle hole in the anchor. The working suture is pinched in a tortuous path that provides a sound lock and prevents sliding of the working suture relative to the anchor once the suture is appropriately tensioned. The strength of the lock is enhanced by the overall tortuous path followed by the working suture when the anchor is pulled against the cortical shell as the working suture goes through several near 90-degree turns which provide increased friction against the toggle body as well as the friction applied by the suture lock.

In some alternative embodiments, a solid or molded locking member is utilized instead of the above-described locking suture. In one embodiment the locking member is affixed to the end of a pull suture. The locking member is movable relative to the toggle body by applying force to the pull suture. In the first position, as the anchor is implanted, the locking member is position with the working suture flossable or slidable therethrough. After tensioning the working suture, the pull suture is tensioned to move the locking member to a second position that locks the working suture in place. This is done by creating a pinched or tortuous path portion for the working suture through the toggle body/locking member combination. It functions in a similar fashion to the above described suture lock.

Each individual anchor includes features that assure it will implant properly through the tendon in a hole punched through the cortical shell of the humeral head. The anchor is inserted lengthwise through this hole into the spongy or cancellous bone. It is pushed by the point of a bone punch that mates with a dimple formed in the proximal end of the implant. The mating surface dimple is shaped to help maintain contact between the anchor and the punch while also allowing the anchor to pivot, rotate, or toggle from an insertion configuration in which the central axis of the anchor is aligned with the central axis of the punch to an implant configuration in which the central axis of the anchor no longer aligns with the central axis of the punch. The rotation or toggling may have two parts: an initial change of axial direction as the anchor passes beyond the cortical shell into the cancellous bone during advancement as the punch is used to push the anchor, and a second change of axial direction under tension applied using the working suture as described below. The cancellous bone varies greatly in properties by location and patient ranging from very soft and porous to hard cellular structures depending upon many patient-specific factors. The included features of the present anchor assure proper toggled retention within the bone over the range of cortical shell and cancellous bone variations.

In selected embodiments, the implant preferably includes an acute angle on the distal surface with the upper side projecting further longitudinally than the lower side. Inserted this way, the longer portion engages the cancellous bone and begins rotation during anchor insertion. With both the distal and proximal portion of the working suture extending up through the bone hole, one can pull the distal working suture selectively, which further rotates the implant body. In some examples the rotation may be to an angle of about 90 degrees relative to the central axis of the bone hole, though this extent of rotation is not necessary to the inventive concept. It has been found that in hard cancellous bone, the pulling on the distal suture at times may not cause rotation because the proximal portion is held rigid by a hard layer of cancellous bone and therefore pulling causes the toggle body to back out of the hole and lie under the tendon. To prevent this, the implant includes a fin or fins on the proximal portion that upon delivery project proximally and radially with a cross dimension greater than that of the bone hole. The size of the fins prevents back out of the anchor but also the fins are located to project and to catch on the cancellous bone and assist in rotation.

The single working suture is pre-strung through a plurality of anchors to be used as a set to form an implanted array having a tensioned suture stitch extending from one anchor to the subsequent anchor in the pre-strung chain. As previously stated, each anchor is slidable or flossable with sufficient force applied to move along the working suture. Each anchor is equipped with a suture lock as described above, except the first anchor in the chain which can have a standard suture lock or a fixed non-slidable suture connection. A chain of anchors can carry in the range of about 8 to 12 anchors in some preferred embodiments.

The high-density array of anchors is formed by implantation of the anchors in a chain or row which can be a relatively straight line or curve depending upon the tear to be repaired at the discretion of the surgeon. A delivery device designed for sequential transtendinous implantation of each anchor in the array includes an elongated tube with a lumen therethrough having an anchor delivery tube therein with a short nub and a bone punch extending from a distal end of the elongate tube and anchor delivery tube. The bone punch extends beyond the short nub in an extended position. In use, the distal end of the three-part assembly (bone punch, nub and elongate tube) which leads with the distal tip of the punch, is positioned at a selected location on top of the tendon as properly positioned on the bone beneath. The assembly is tapped so that the punch penetrates the tendon and the bone while the nub follows and extends into the bone hole at least a short distance. The assembly is inserted until the distal end of the elongate tube is in desired contact with the tendon surface. At this point the punch is withdrawn proximally while the nub maintains registration with the formed hole and the elongate tube is pressed against tendon surface. A first anchor is loaded into the elongate tube proximal portion and the punch is again moved distally to force the first anchor/implant down the tube through the tendon along the nub and into the bone. The nub functions like a shoehorn to track the anchor through the spongy tissue of the tendon that has closed around the nub.

Once the first anchor is inserted to the full depth of the punch pin, the punch pin is removed. This action also releases the nub so that it can move proximally into the tube if needed as the implanted anchor is rotated and moved up against the inner cortical shell. A particularly designed implantation tool may be used to manage nub retraction in some examples, and may apply a positive force to retract the nub after the anchor has been passed therethrough. With the punch pin (and in some examples, the nub) retracted, the distal suture is pulled to further rotate the toggle body and move it toward the cortical shell. The working suture may be locked into position relative to the first anchor using the locking suture or locking member prior to pulling the distal suture, or even prior to starting implant, if desired. When the first anchor is set in sufficiently strong material inside the bone (which can be harder cancellous bone or may be resting against the under surface of the cortical shell) the delivery device can be moved for implantation of the next anchor.

With the second and subsequent anchors, both a proximal and a distal suture portions of the working suture extend up through the delivery device. It is the distal portion of the working suture that is pulled to cause rotation of the anchor while also allowing the working suture to slide through the one or more holes in that anchor and the slack extending to the previous anchor is therefore shortened. It is also recognized that the proximal portion of the working suture can be tensioned in some embodiments to aid in rotating and seating the anchor in proper position within the bone hole. During toggling of the anchor and subsequent tensioning of the working suture, the distal end of the delivery tool may be pressed against the tendon to provide a counterforce against pullout. This is continued until the properly tensioned suture stitch is formed at which point the locking member or locking suture on the second or subsequent anchor is activated to maintain tension in the individual suture stitch. The locking suture proximal extension can be cut off after tightening or a selectively breakable suture can be used and such breakable portion is positioned proximate the slidable knot. For versions with the locking member, the suture attached to the locking member may be cut or may also have a weakened portion to allow break-away. This is repeated for a desired number of anchors in the pre-strung chain which as implanted form a high-density array as described above.

As can be understood, the number of suture stitches formed is equal to the number of anchors in the chain implanted minus 1. Further, the string of stitches is continuous with each stitch tensioned and locked independently to form a required robust tendon attachment. The continuous string of stitches can form a row or chain of stitches of desired shape such as a linear row, a zig-zag shape, an arc, etc. By row or chain, it is meant that the suture stitches extend from one anchor to the next in the sequence of implanted anchors.

As previously stated, the distance between ends of a suture stitch (the distance between anchors) is less than about 7 mm (less than about 10 mm from center of bone hole to center of bone hole) to provide consistent force on the tendon against the bone to reduce creep. One particularly robust array of implanted anchors includes a first array implanted in a medial portion of the original tendon footprint to form a row or line of stitches generally perpendicular to the length or direction of the tendon's forces. A second array can then be implanted laterally nearer the edge of the tear with at least one anchor through the tendon while at least one other anchor is implanted laterally of the tendon edge to reapproximate the tendon properly against the bone. The lateral row can be implanted in a zig zag pattern or other appropriate pattern based on the shape of the tear. Depending upon tear size and location, multiple patterns can be utilized.

As becomes clear in the above description, the pre-strung array of anchors in combination with the working suture and multiple locking sutures creates a strong need for a device that manages the anchors and their attendant sutures or suture sections to maintain orderly implantation, use and sterility during a procedure. Further, the small size of the anchors necessitates some sort of holder for individual anchors. Applicants disclose herein a cartridge for an anchor array or chain that is made up of individual anchor holders. Within each holder the anchor is releasably attached and held in a fixed position with proximal and distal working suture portions plus the suture lock or suture attached to the locking member pre-strung on the anchor. The ends of the proximal and distal working suture portions pass either to the next or prior holder as appropriate. The length of proximal suture lock material, or extra length of the suture attached to the locking member is preferably stacked or coiled within the holder with a proximal end attached to the holder. Further, the internal structure of the holder includes at least one projecting boss that keeps the threaded proximal and distal suture in near perpendicular alignment with the through hole(s) and provide a bearing surface that makes for easy flossing of the held anchor along the length of the working suture. The individual holders can be coupled to a loading chamber on the above-described delivery system to allow easy transfer of the anchor into the delivery tube while managing the pre-strung sutures and locking suture.

The present application is specifically directed to features and designs of the toggle body implant in combination with various embodiments of a flossing working suture passing therethrough that make possible tensioning of the working suture that runs from one toggle body to the next in the array. The application further discloses various locking mechanisms to lock the working suture as tensioned to complete a tensioned independent stitch between successive anchors. The specific features below should be studied in conjunction with the overall system to adequately assess each improvement.

In one representative embodiment, the toggle-type suture anchor includes an elongated toggle body having at least a first hole through the toggle body extending from a first longitudinal surface to a second longitudinal surface. A suture passes into the first hole at the first longitudinal surface and out the first hole at the second longitudinal surface, wherein the suture is adapted to slide through the first hole when a force is applied thereto. Additional there is included a locking loop which encircles the suture proximate the second longitudinal surface adjacent the elongated toggle body, the locking loop being adjustable between a first position allowing the suture to slide through the locking loop and a second position engaging the suture and preventing sliding within the locking loop and preventing sliding of the suture through the first hole in one direction.

The toggle-type suture anchor can also, in some examples, include a second hole through the elongated toggle body extending from the first longitudinal surface to the second longitudinal surface at a spaced interval along the elongated toggle body relative to the first hole. In this embodiment the suture can exit the first hole at the second longitudinal surface, extend into the second hole on the second longitudinal surface and exit the second hole at the first longitudinal surface. This routing leaves a length of suture extending adjacent the toggle body between the first hole and the second hole near the second longitudinal surface with the locking loop encircling this length of suture.

In some embodiments, the toggle-type suture anchor can include a third hole through the toggle body extending from the first longitudinal surface to the second longitudinal surface and located between the first and second holes. The locking loop can be mounted through and extend from the third hole at the second longitudinal surface after passing through the toggle body. The locking loop can be a cord having a free end extending through the third hole and beyond the first longitudinal surface, the cord having at least a slidable knot tied therein to allow collapsing of the locking loop from the first position to the second position when the free end is tensioned. The locking loop can include any type of collapsible loop which tightens upon pulling of the free end of a cord which may include one-way barbed sutures, zip tie type ratchet structures or other mechanisms.

In some alternative embodiments, the suture can be routed through the toggle body in a different pattern. With a toggle body having a second hole through the elongated toggle body extending from the first longitudinal surface to the second longitudinal surface at a spaced interval along the elongated toggle body relative to the first hole, the suture exiting the first hole at the second longitudinal surface can wrap around the elongated toggle body over the top of the suture extending from the first hole, first longitudinal surface then into the second hole through the first longitudinal surface and out the second longitudinal surface. This forms a one-way locking knot preventing the suture from sliding or increasing friction in one direction but allowing sliding in the other direction. The locking loop can encircle at least one of the overlapping sutures proximate their intersection. Alternatively, the locking loop can encircle both of the overlapping suture portions proximate their intersection.

Alternatives to the locking loop are also included in some embodiments. The toggle-type suture anchor can include an elongated toggle body having at least a first hole through the toggle body extending from a first longitudinal surface to a second longitudinal surface. A suture passes into the first hole at the first longitudinal surface and out the first hole at the second longitudinal surface, wherein the suture is adapted to slide through the first hole when a force is applied thereto. In this embodiment a locking member is included which at least partially encircles the suture proximate the second longitudinal surface adjacent the elongated toggle body. The locking member is moveable between a first position allowing the suture to slide through the locking member and a second position preventing the suture from sliding through the locking member in at least one direction. The locking member can be slidably received in a chamber formed in the elongated toggle body and in the first position has a portion spaced radially from the longitudinal surface to allow suture movement while in the second position the locking member is held deeper within the chamber and creates a pinched tortuous pathway for the suture to prevent suture movement.

In the locking member embodiment, the toggle body can also include a second hole through the elongated toggle body extending from the first longitudinal surface to the second longitudinal surface at a spaced interval along the elongated toggle body relative to the first hole wherein the suture exiting the first hole at the second longitudinal surface extends into the second hole on the second longitudinal surface and exits the second hole at the first longitudinal surface with a length of suture extending adjacent the toggle body between the first hole and the second hole near the second longitudinal surface encircled by at least a portion of the locking member. In this embodiment, the locking member can be slidably disposed in a chamber formed into the elongated body wherein it is movable between the first and second position. In the first position the locking member can be positioned adjacent the elongated body longitudinal surface to allow suture movement and in the second position pulled into the chamber sufficient to create a pinched or tortuous path that prevents movement of the suture in at least one direction.

As with some other embodiments, the toggle body can include a third hole through the toggle body extending from the first longitudinal surface to the second longitudinal surface and located between the first and second holes, wherein the locking member further comprises a pull suture extending from the locking member through the third hole at the first longitudinal surface after passing through the toggle body.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present invention includes multiple components, devices and methods to create and use an overall system for reattaching soft tissue to bone. It is particularly useful to create a robust repair of avulsed or torn tendons, such as the supraspinatus tendon, in an arthroscopic rotator cuff repair. The implants and delivery devices make possible a more efficient and reproducible anatomical repair which should have more success (i.e., lower failure rate) than current techniques. The tendon is securely attached and held with adequate force to its original footprint with very little creep during movement of the joint. This may decrease the need for a patient's shoulder to be immobilized in a sling, increase the rate of healing reattachment of tendon to bone and allow early physical therapy to idealize postoperative shoulder range of motion and strength.

The implanted array of anchors with a continuous set of anchor-to-anchor single suture stitches creates a seam-like attachment akin to a sewing machine construct. Further, the small cross-sectional size of the anchors (less than 3 mm in diameter) allows the anchors to be placed in close proximity to one another (less than about 7 mm between adjacent anchors). This creates a very stable anchor-to-anchor suture stitch. Combining this concept with the disclosed anchor design allows the suture stitch to be tightened and locked individually when the adjacent suture anchors are implanted. This can be repeated many times to implant a row of anchors with continuous independently tensioned and locked sutures between adjacent anchors. Also, because the anchors are in a high-density array, the tension force components on the tensioned suture are more vertically applied to the top surface of the tendon (or other connective tissue) to thereby compress the tendon firmly against the footprint of the bone without creep or slippage during joint movement which idealizes the tendon healing environment.

FIGS. 1A-1K are a series of illustrations of exemplary toggle bodies or toggle-type anchors that can be used in a procedure for attaching tendon to bone. The illustrations also show a single working suture slidably disposed in passages through the anchor and through a locking loop. The locking loop is configured to have an open position allowing movement of the single working suture, and a closed or locked position that prevents movement of the single working suture.

Figure 1A:
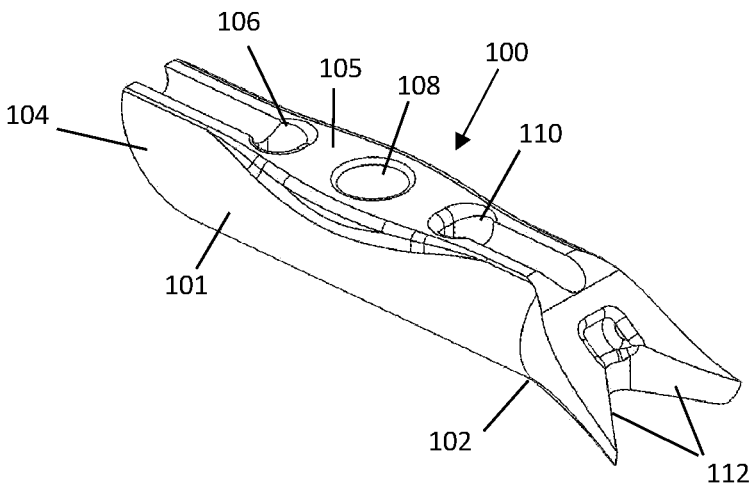
FIG. 1A is a perspective view of a representative toggle body.

Referring to FIG. 1A, a perspective view of a representative anchor in the form of a toggle body 100 is illustrated. The toggle body 100 can be an elongate body 101 having a length defined by a proximal end 102 and a distal end 104. The elongate body 101 can be a generally cylindrical body but other shapes are possible. For example, as shown in FIG. 1A, the toggle body 100 is generally cylindrical but the top surface 105 and bottom surface 107 have flat axially extending surfaces that allow room for sutures when the toggle body 100 is in a round delivery tube. The length of the toggle body 100 is substantially longer than the diameter thereof, thus allowing the toggle body 100 to be inserted lengthwise or axially into a small bone hole. Once inserted, unlike most anchors used today, the entire body is pivoted or toggled so that it stays within the bone and has substantially its entire length compressed against material inside the bone. That is, the longitudinal axis of the toggle body 100 is rotated or pivoted from the direction used to insert through the bone hole, thereby preventing removal. This approach means that removal would require the anchor itself to fail, rather than simply it being released (or "pulled out") from surrounding tissue, thus providing improved pullout strength (greater than 600 N before anchor failure when implanted in the array disclosed herein) from an anchor requiring a very small insertion hole (less than about 3 mm). As previously stated, and described in detail below, small insertion holes allow much closer placement of anchors in a high-density array.

The toggle body 100, can have a length of about 6 mm to about 10 mm in some embodiments. This length gives adequate strength while leaving enough room inside the bone for the high number of anchors implanted. The toggle bodies are preferably molded or machined from a polymeric material, preferably a high tensile strength material such a poly-ether-ether ketone (PEEK) which is highly biocompatible. In applications where MRI imaging would not be an issue, metal can be utilized in part or all of the toggle body.

Figure 1B:
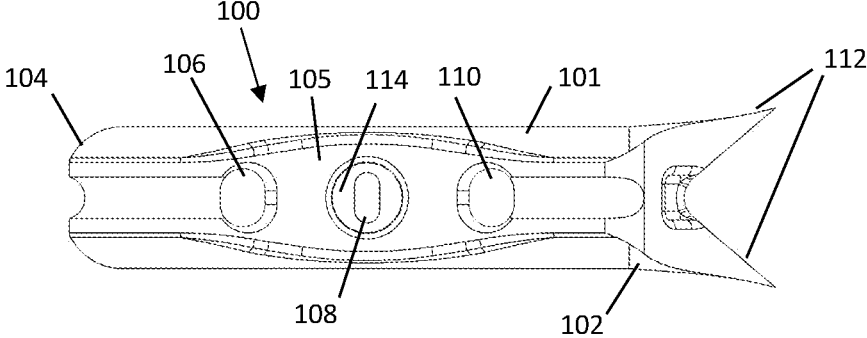
FIG. 1B is a top view of the toggle body of FIG. 1.
Figure 1C:
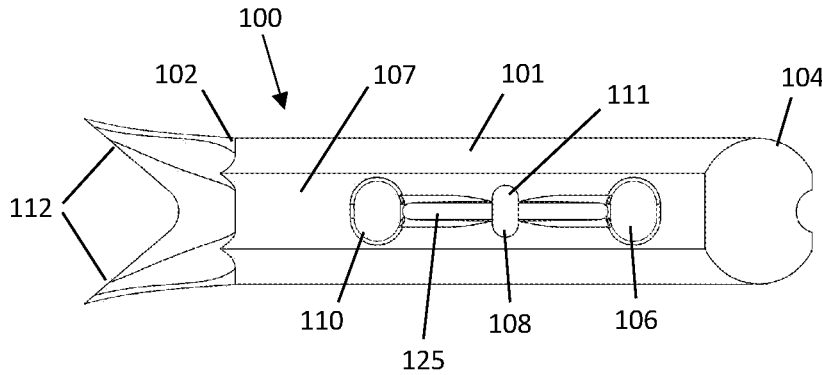
FIG. 1C is bottom view of the toggle body of FIG. 1.
Figure 1D:
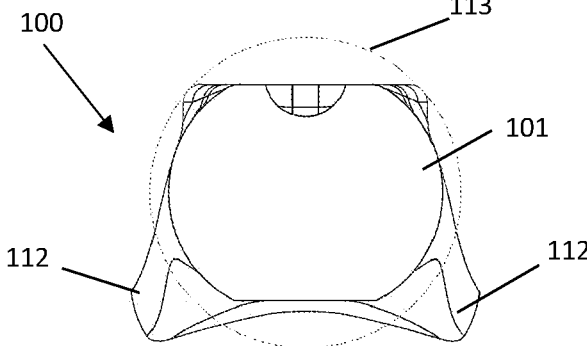
FIG. 1D is a distal end view of the toggle body of FIG. 1.
Figure 1E:
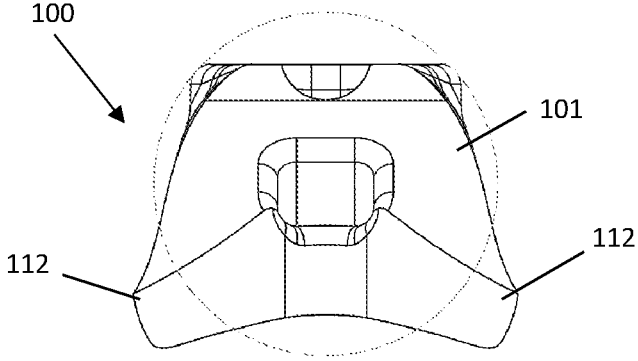
FIG. 1E is a proximal view of the toggle body of FIG. 1.

Referring now also to FIGS. 1B and 1C it can be seen that the toggle body 100 can include a number of holes or passages through the cross section of the toggle body 100. As illustrated, the toggle body 100 has a proximal bore or passage 110, a middle passage 108 and a distal passage 106. The passages 106, 108, 110 extend from the top surface 105 to the bottom surface 107 such that the passages 106, 108, 110 extend through the cross section of the elongate body 101. In other embodiments, the toggle body may have fewer or more bores or passages, such as having a single bore, two bores, or more than three bores. In the illustrated embodiment, the proximal passage 110 and distal passage 106 receive a portion of a common working suture slidable with respect to the toggle body 100 during use. The middle passage 108 receives a locking suture which is independent for each anchor used in an array of anchors.

The distal end 104 of the toggle body 100 has an angled surface. As shown, the angled surface creates a longer upper longitudinal surface 105 than lower longitudinal surface 107. In other words, the upper surface projects a greater distance distally than the lower surface. This is useful during insertion of the toggle body 100 because the projecting distal surface plows into cancellous spongy bone when implanted to initiate at least partial rotation of the toggle body during insertion. Keeping in mind that the present toggle bodies 100 are preferably implanted through the tendon, it is important that the toggle body 100 toggle every time or it may pull out of the bone hole under tension yet not be visible due to its position beneath the tendon.

The proximal end 102 of the toggle body 100 can include one or more projecting fins 112. The illustrated embodiment includes two fins 112. Each fin 112 projects outward and proximally. Further, in some embodiments, as depicted, the fins 112 project downward as they extend proximally. The function of the fins 112 is best understood with reference to FIGS. 1D and 1E which are distal and proximal end views of the toggle body 100, respectively. A reference circle 113 is included which indicates the general maximum cross section or diameter of the elongate body 101. The bone hole in which the implant will be placed is sized to closely match this dimension, as is the inner diameter of a delivery tube used to deliver the implant. In contrast, as shown, the fins 112 each project laterally beyond the outer cross section or diameter of the elongate body. During insertion the fins 112 flex inward under compressive force due to contact with the inner diameter of a delivery tube to fit in the bone hole.

Figure 1F:
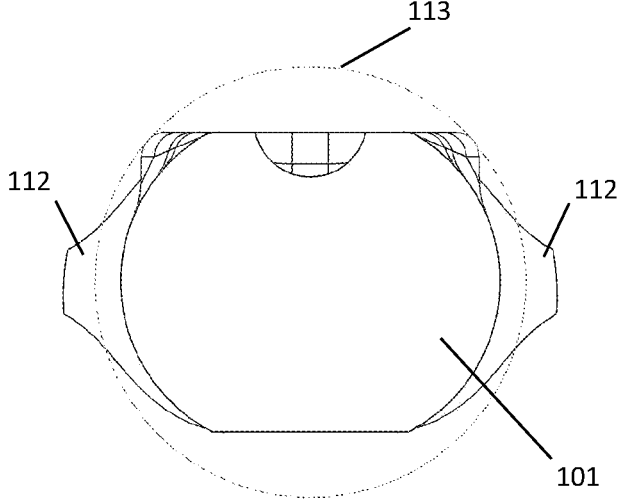
FIG. 1F is a view of an alternative fin orientation in a toggle body.
Figure 1G:
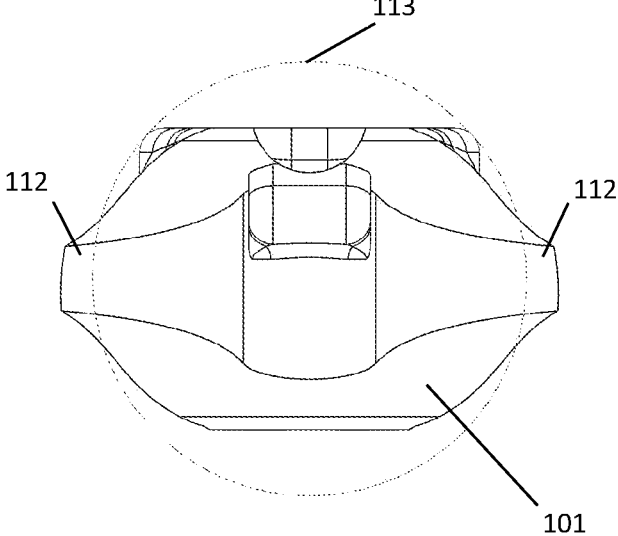
FIG. 1G is another alternative fin orientation in a toggle body.

Once delivered and released from compressive forces of the delivery tube, the fins 112 relax to a size greater than the bone hole. In some embodiments, each fin tip extends about an additional 0.5 mm beyond the size of the bone hole where that feature is inserted. Such fin tips may be described as extending about 0.5 mm beyond the maximum outer diameter of the rest of the anchor body, for example, in the range of 0.4 mm to 0.7 mm. This feature provides an added safeguard against the toggle body 100 dislodging or backing out of the bone hole under tension if the toggle body 100 has not adequately toggled. Further, the fins 112 are positioned so that tension on the toggle body 100 causes the partially toggled anchor to grab cancellous bone and further rotate the anchor. Alternative designs of the fins 112 are also depicted in FIGS. 1F and 1G. The fins 112 in these figures have alternative positions on the elongate body 101 and direction of proximal extension. The fins 112 of FIG. 1F are widest at a centrally located position to keep the anchor centered in the delivery tube since the largest dimension is horizontal at the diameter of the tube during delivery.

The top and bottom views of FIGS. 1B and 1C show details of the proximal 110, middle 108 and distal 106 passages. In particular, the middle hole has a platform 114 formed within the elongate body 101, part way through the cross section. That is, in this example, the middle passage 108 has a change in size or shape partway along its length, to define a platform 114. From the bottom view, it can be seen that the middle passage 108 continues from the platform 114 with a slotted or oval shape or portion 111, while having a circular profile from the top view. The function of these passages is detailed in the cross-section perspective views of FIGS. 1H and 1I wherein representative cords or sutures 115, 116 have been pre-strung on the toggle body 100.

Figure 1H:
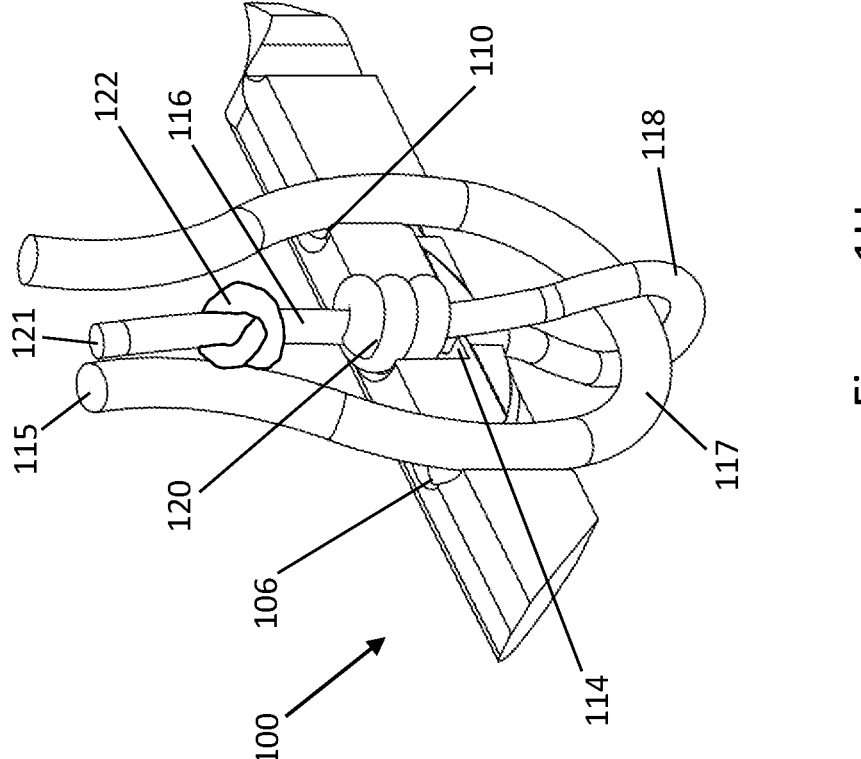
FIG. 1H is partial cut-away view of the toggle body of FIG. 1 having a working suture and locking suture in an open position illustrated.

First, there is a single suture, called herein the working suture 115 that extends into the proximal passage 110 from the top surface, and extends out at the bottom surface. The working suture 115 then extends up through the distal passage 106 from the bottom surface and out through the top surface. This leaves a section 117 of the working suture 115 extending past or adjacent the middle passage 108 along the bottom surface. The working suture 115 can be flossed or is slidable as threaded through the distal 106 and proximal passage 110, meaning the toggle body 100 can slide on the suture when tension is applied. Second there is a locking loop 118 that encircles a portion of the section 117 of the working suture 115 extending adjacent the outer surface of the toggle body 100 between the proximal 110 and distal 106 passages. The locking loop 118 has a first open position as depicted in FIG. 1H wherein the working suture 115 is free to slide through the locking loop 118 and a second closed position depicted in FIG. 1I wherein the locking loop 118 engages the section 117 and prevents it from sliding within the locking loop 118 after the suture is appropriately tensioned.

Several examples refer to a suture, cord, or thread, which can be used as the working suture 115 or in the locking loop 118. These elements may be, for example, made of natural material such as silk and/or synthetic materials such as polyglycolic acid, polylactic acid, and polydioxanone, each of which are known for use as absorbable sutures, and/or nylon and polypropylene, which are typically non-absorbable. Various coatings, including antimicrobial, anti-wicking or lubricious coatings may be applied as well. More broadly, these elements 115, 118 may include any item that can be used to couple together objects in a surgical environment, such as any sufficiently biocompatible metal, natural material, plastic or other artificial material adapted for use in a surgical procedure. Monofilaments or more complex structures including braids, weaves, windings, twisted threads, coated or multilayer member, etc. may be used.

In the embodiment depicted, the locking loop 118 extends from the bottom surface of the toggle body 100 through the middle passage 108. The locking loop 118 includes a cord or suture having at least a slidable knot 120 tied therein to allow collapsing of the locking loop 118 when a free end or proximal end 121 of the suture lock 116 extending through the middle passage 108 is tensioned. As shown, the upper portion of the middle passage 108 is sized to receive at least a portion of the slidable knot 120 therein. The slidable knot 120 then contacts the surface of the platform 114 which does not allow the knot to pass through towards the bottom opening. The lower oval portion 113 of the middle passage 108 is a slot or oval which allows both legs of the locking loop 118 to pass therethrough, preferable side by side in the slot direction. The interaction of these components locks the working suture 115 with respect to the toggle body 100 after the working suture 115 is appropriately tensioned. As shown, especially seen in FIGS. 1C and 1I, the bottom of the toggle body 100 includes a channel 125 formed in the bottom surface 107 between the proximal 110 and distal 106 passage. When the working suture 115 is tensioned, it is pulled up into this channel 125 which is sized to make the suture less able to floss or move therethrough by increasing frictional resistance to such movement but does not fully lock the suture. Further, the working suture then has two near 90-degree angle turns at the bottom openings of the distal 106 and proximal 110 passage which also make it more difficult to floss but does not fully lock the working suture 115. The locking loop 118 closing around the working suture 115 and pulling it toward and at least partially into the slot or oval portion 113 is the structure that ultimately locks the suture so that cumulative friction prevents slippage of the working suture 115.

In the illustrative example shown in FIGS. 1H to 1K, the free end 121 of the suture lock 116 is configured to break away from the locking loop 118 proximal of the sliding knot 120. A break knot is illustrated at 122 and is one example of a way of introducing weakness in the suture lock. The break knot 122 is located a distance above the sliding knot 120, sufficient that when the suture lock 116 breaks away, the sliding knot 120 remains intact and secure; for example, 3 to 10 mm proximal of the sliding knot, or more or less. Rather than a break knot 122, a nick or other point of weakness may be imparted at the desired or preferential point of failure in the suture lock 116.

Figure 1I:
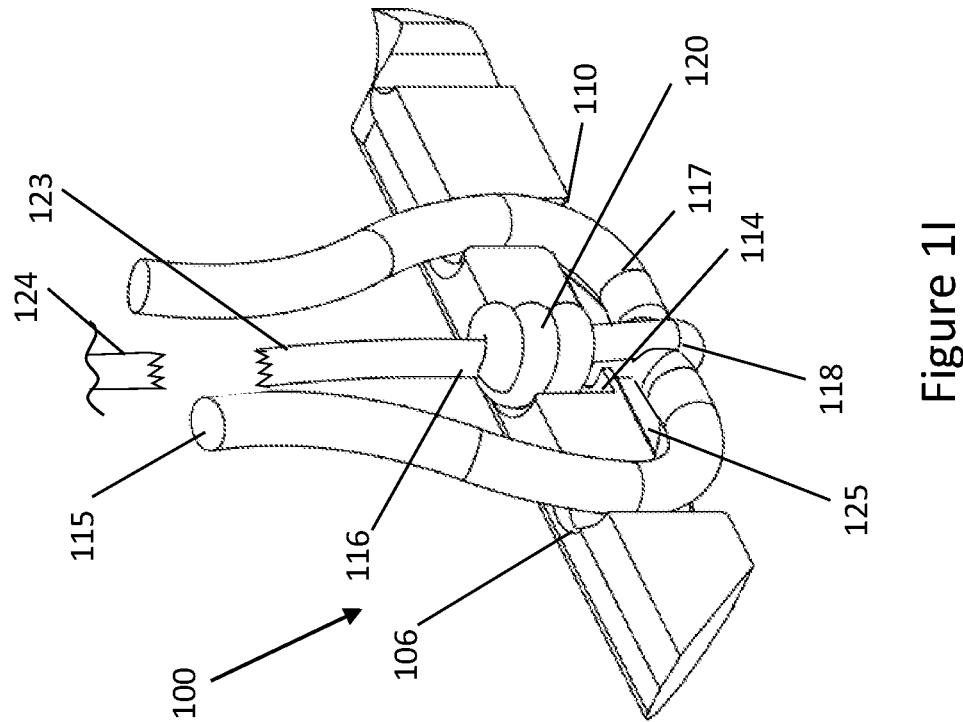
FIG. 1I is partial cut-away view of the toggle body of FIG. 1 having a working suture and locking suture in a closed position illustrated.
Figure 1J:
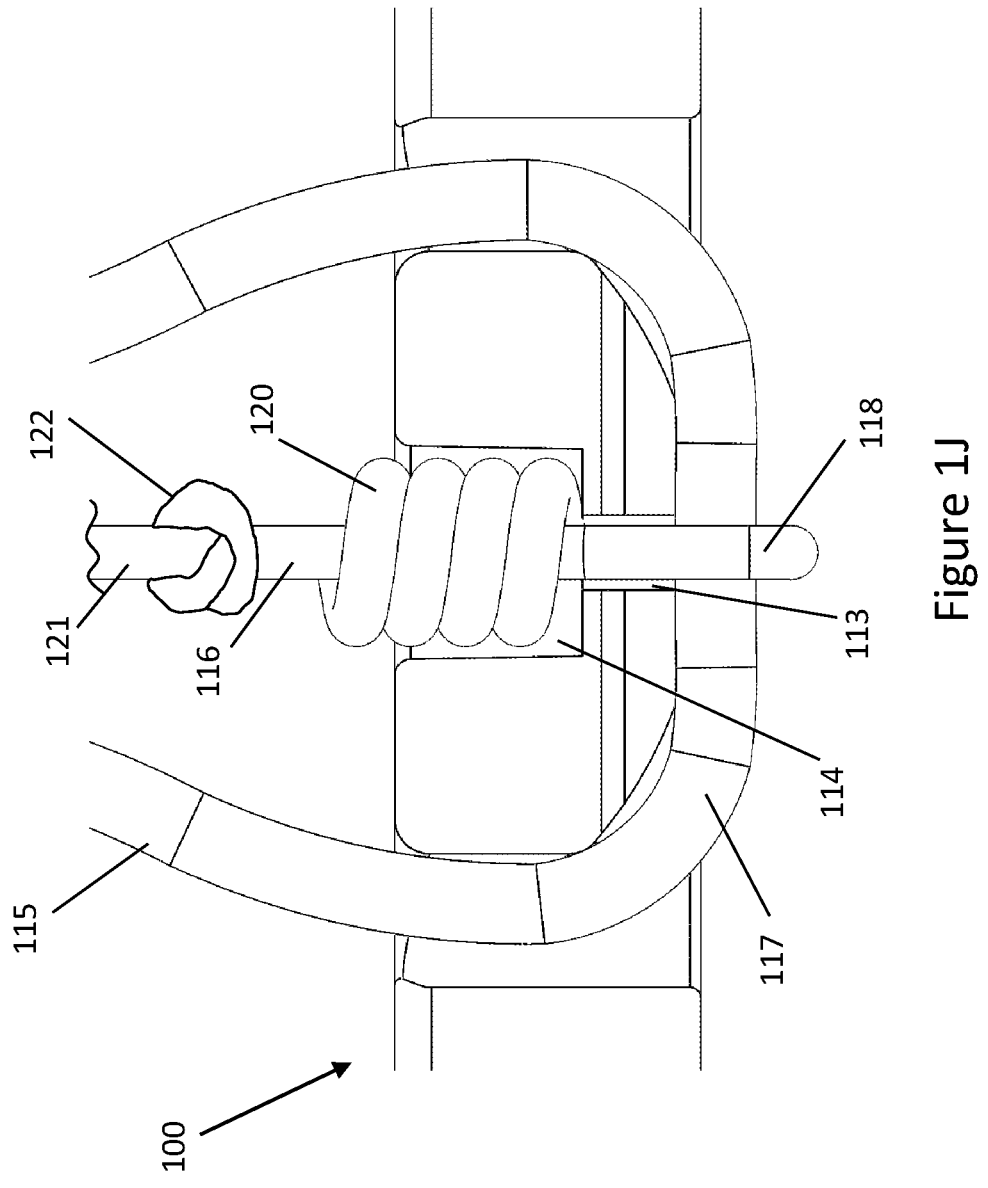
FIG. 1J is a schematic illustration of the interaction between the locking suture and the working suture.
Figure 1K:
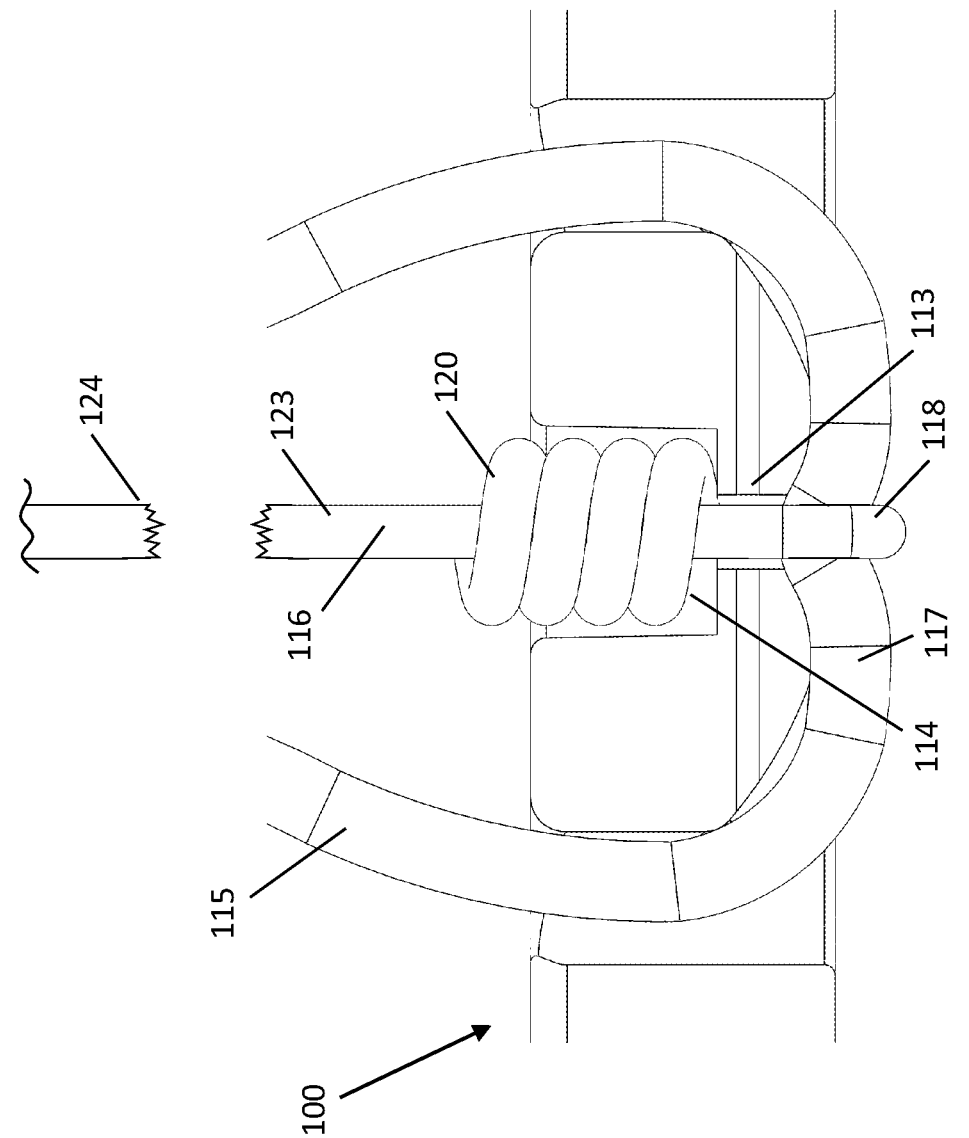
FIG. 1K is a schematic illustration of an alternative interaction between the locking suture and the working suture.

FIGS. 1J and 1K depict the way in which the locking loop 118 pulls the section 117 of the working suture 115 into the oval portion 113 in two different embodiments. The degree to which the section 117 of the working suture 115 enters the slot 113 will be dependent upon how tight the loop is closed, the size of the locking suture and the size of the slotted opening. In preferred embodiments, at least a portion of the cross section of the working suture 115 is pulled into the slot so that the edge surfaces of the slot walls provide significant friction and aid in locking. In another example, the preferential point of failure is designed to allow the locking loop 118 to be drawn into the slot before the failure occurs.

The locking loop 118 in combination with the design of the middle passage 108 is an assembly for locking a slidable working suture 115 when tensioned in a suture toggle body 100 during tissue fixation to bone. The locking loop 118 encircles a portion of the working suture 115, wherein collapsing the locking loop 118 compresses the cross section of the working suture 115 to lock the working suture 115 when tensioned. The suture lock 116 is preferably formed of a suture having at least a slidable knot 120 tied therein to form the loop 118 to allow collapsing of the loop 118 when a tightening leg 121 through the second passage 108 is tensioned. The second passage 108 has an upper portion for receiving the slidable knot 120 at least partially therein that terminates in a platform 114 within the toggle body 100 that does not allow passage of the slidable knot. The second passage includes a lower portion having an oval shape for allowing both legs of the locking loop to pass therethrough side by side and out the passage. A particularly preferred knot is a 4-throw uni knot. However, other slidable knots 120 may be used, as desired. Further, the second passage oval portion is sized to allow movement of at least a portion of the working suture 115 to be pulled therein in response to tension on the locking cord. The working suture 115 is preferably a braided multistrand suture having a compressible cross-sectional area that reduces by at least about 25% when the locking loop is tightened during use. The working suture 115 may be a round No. 2 suture in some embodiments. Other size and type sutures may be used.

As also shown in FIGS. 1I and 1K, after the sliding knot 120 is tightened, and the working suture is drawn at least partly into the slot, the preferential point of failure in the locking loop 116 (such as the break knot or nick described above) breaks, leaving free tail at 123 on the locking loop, a distance above the sliding knot, while the rest of the proximal portion of the suture lock 124 can be discarded. In some examples, a more proximal portion of the suture lock is secured to a cartridge, so that a physician may cause the suture lock to break as shown by pulling on the cartridge itself. In an example, the preferential point of failure is designed to allow tightening of the locking loop 118 onto the working suture 115 before the failure occurs. For example, the locking loop and the preferential point of failure may be configured for breaking under a pull strength in the range of 3-10 pounds of force, more preferably, 5-7 pounds of force, or more or less as desired. The pull strength needed to tighten the locking loop 118 onto the working suture may be less than the pull strength needed for breaking the preferential point of failure in some examples by, for example, an amount in the range of 0.5 to 3 pounds, or 0.75 to 2 pounds, or about 1 pound.

Alternative designs can be utilized for the toggle body described above along with variations in the routing of the working suture and location of the locking loop or alternative locking mechanisms. FIGS. 2A through 2L detail several of these alternatives discussed in detail below.

Figure 2A:
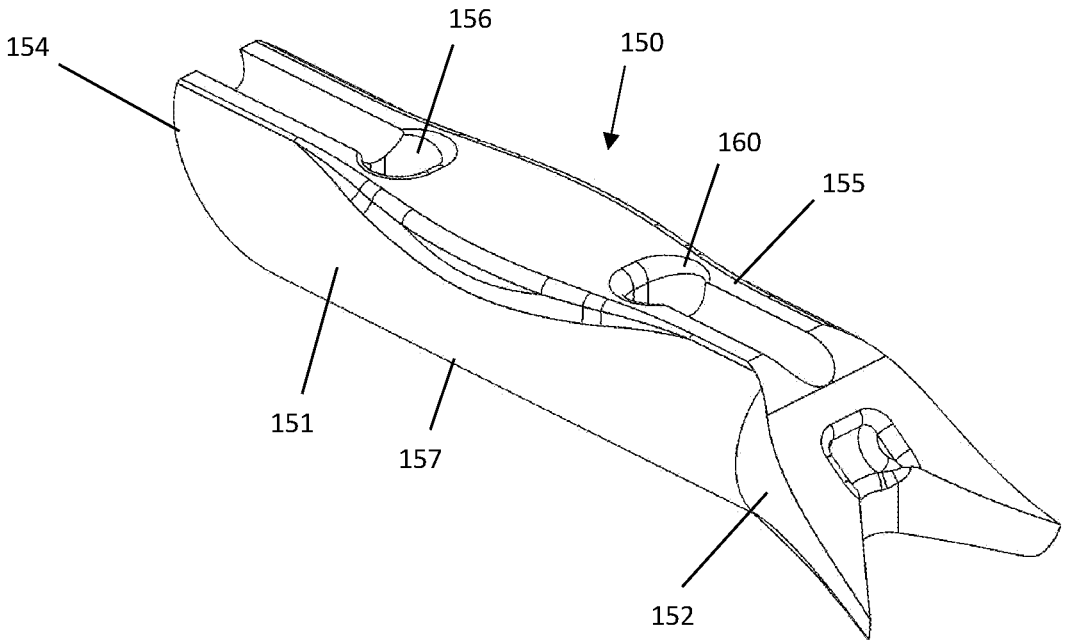
FIG. 2A is a perspective view of an alternative toggle-body design.

Referring to FIG. 2A, a perspective view of an alternative representative anchor in the form of a toggle body 150 is illustrated. The toggle body 150 can be an elongate body 151 having a length defined by a proximal end 152 and a distal end 154. The elongate body 151 can be a generally cylindrical body but other shapes are possible. For example, as shown in FIG. 2A, the toggle body 150 is generally cylindrical but the top surface 155 has a flat axially extending surface that allows room for sutures when the toggle body 150 is in a round delivery tube. The length of the toggle body 150 is substantially longer than the diameter thereof, thus allowing the toggle body 150 to be inserted lengthwise or axially into a small bone hole. Once inserted, unlike most anchors used today, the entire body is pivoted or toggled so that it stays within the bone and has substantially its entire length compressed against material inside the bone. That is, the longitudinal axis of the toggle body 150 is rotated or pivoted from the direction used to insert through the bone hole, thereby preventing its dislodging. This approach means that failure would require the anchor itself to fail, rather than simply it being released (or "pulled out") from surrounding tissue, thus providing improved pullout strength (greater than 600 N before anchor failure when implanted in the array disclosed herein) from an anchor requiring a very small insertion hole (less than about 3 mm). As previously stated, and described in detail below, small bone holes allow much closer placement of anchors in a high-density array.

The toggle body 150, can have a length of about 6 mm to about 10 mm in some embodiments. This length gives adequate strength while leaving enough room inside the bone for the high number of anchors to be implanted. The toggle bodies are preferably molded or machined from a polymeric material, preferably a high tensile strength material such as PEEK, which is highly biocompatible. In applications where MRI imaging would not be an issue, metal can be utilized in part or all of the toggle body.

Unlike the toggle body of FIG. 1A, the present toggle body 150 includes two holes through the cross section instead of three. As illustrated, the toggle body 150 has a proximal bore or passage 160 and a distal passage 156. The passages 156, 160 extend from the top surface 155 to the bottom surface 157 such that the passages 156, 160 extend through the cross section of the elongate body 151. As with the toggle body of FIG. 1A, the present toggle body 150 includes a distal end with an acute angle and a proximal end with projecting fins. These features provide the same aid in assuring toggling during insertion and subsequent tensioning of the anchor as described previously.

In the illustrated embodiment, the proximal passage 160 and distal passage 156 receive a portion of a common working suture 165 slidable with respect to the toggle body 150 during use. This is illustrated in the cross section view of FIG. 2B. The working suture 165 extends into the proximal passage 160 from the top surface and extends out at the bottom surface. The working suture 165 then extends up through the distal passage 156 from the bottom surface and out through the top surface. This leaves a section 167 of the working suture 165 extending past or adjacent the bottom longitudinal surface between the passages. The working suture 165 can be flossed or is slidable as threaded through the distal 156 and proximal passage 160, meaning the toggle body 150 can slide on the suture when tension is applied. Second there is a locking loop 168 that encircles a portion of the section 167 of the working suture 165 extending adjacent the outer surface of the toggle body 150 between the proximal 160 and distal 156 passages.

Figure 2B:
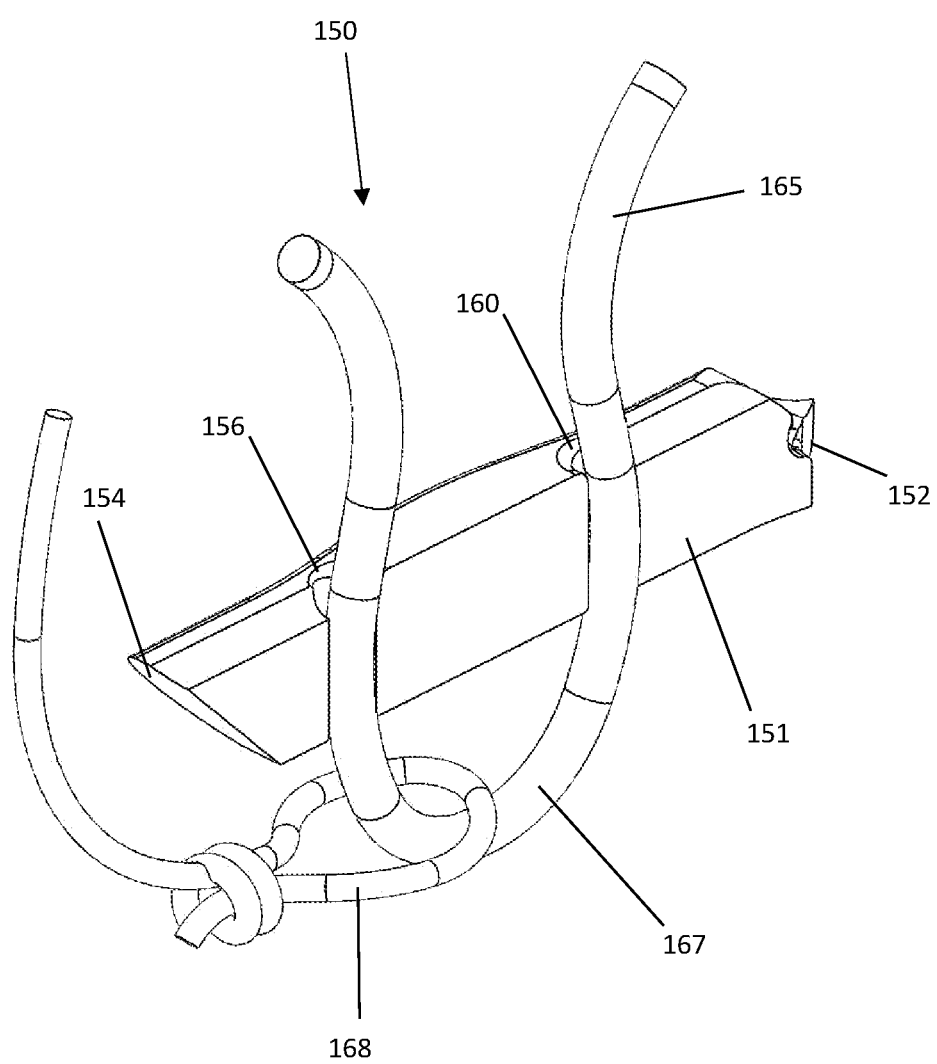
FIG. 2B is a partial cross section of the toggle-body design of FIG. 2A with a working suture and locking loop depicted.
Figure 2C:
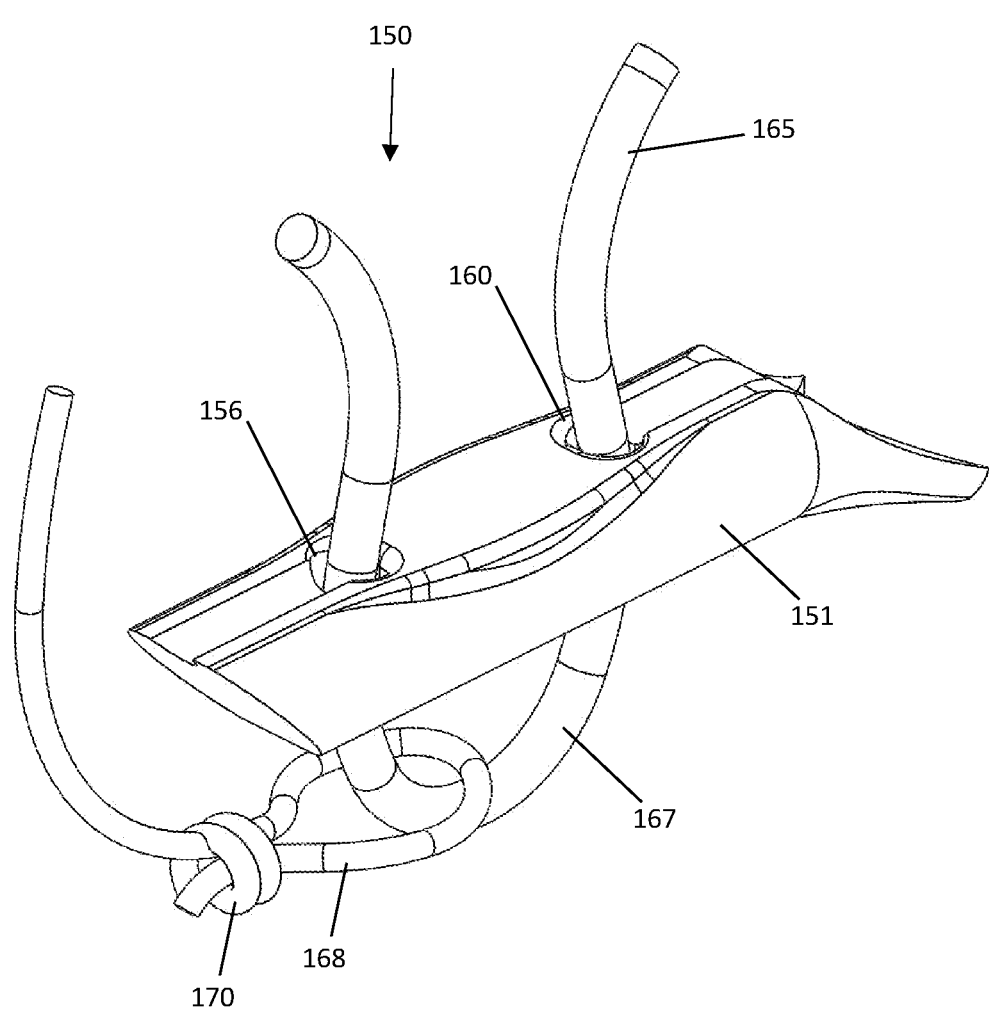
FIG. 2C is perspective view of the embodiment of FIG. 2B.
Figure 2D:
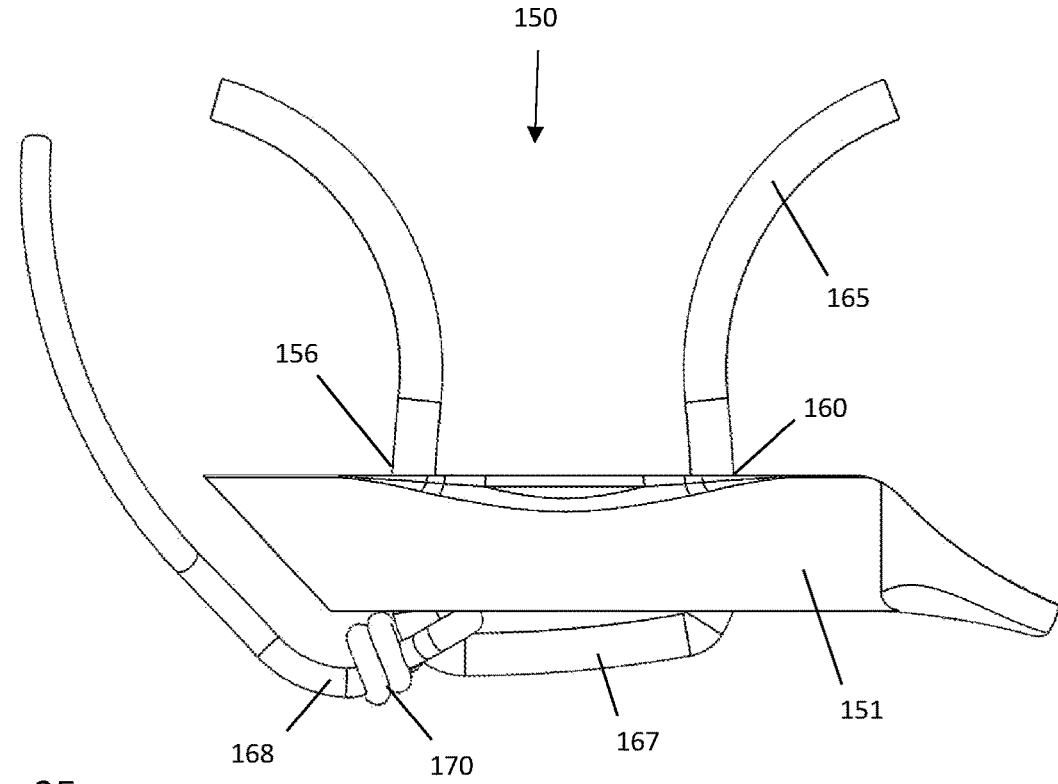
FIG. 2D illustrates the embodiment of FIG. 2C with the locking suture collapsed to lock the suture relative to the toggle body.

The locking loop 168 has a first open position as depicted in FIG. 2B and in perspective view in FIG. 2C wherein the working suture 165 is free to slide through the locking loop 168 and a second closed position depicted in FIG. 2D wherein the locking loop 168 engages the section 167 and prevents it from sliding within the locking loop 168 after the suture is appropriately tensioned. As with previous embodiments, the suture, cord or thread used as working suture or locking suture can be selected from known materials described previously. The free end of the locking loop may include a preferential point of weakness as illustrated previously to allow tightening of the locking loop 168 followed by breaking and removal of the free end.

Unlike the embodiment of FIG. 1A-1K, the present embodiment does not have a third hole through which the locking suture extends, nor can this embodiment pull the working suture into a formed groove that aids in locking the suture. Instead the bulk of the slip knot 170 is intended to act as the stop for locking the tensioned working suture. A particularly preferred knot is a 4-throw uni knot. However, other slidable knots 170 may be used, as desired. The working suture 165 is preferably a braided multistrand suture having a compressible cross-sectional area that reduces by at least about 25% when the locking loop is tightened during use. The working suture 165 may be a round No. 2 suture in some embodiments.

Figure 2E:
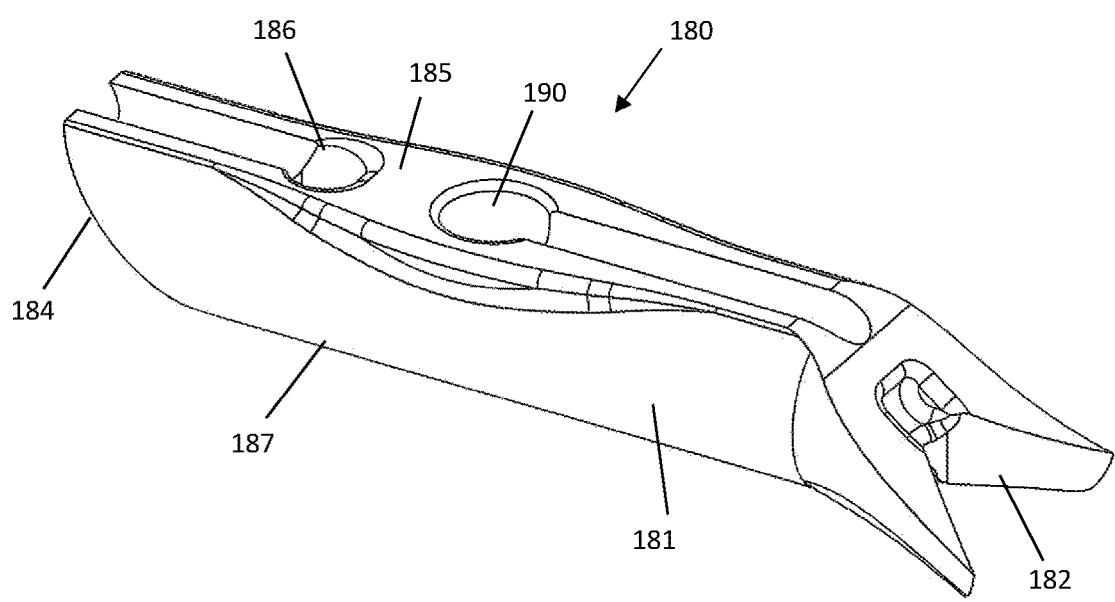
FIG. 2E is a perspective view of another alternative toggle-body design.

Referring to FIG. 2E, a perspective view of another alternative representative anchor in the form of a toggle body 180 is illustrated. The toggle body 180 can be an elongate body 181 having a length defined by a proximal end 182 and a distal end 184. The elongate body 181 can be a generally cylindrical body but other shapes are possible. For example, as shown in FIG. 2E, the toggle body 180 is generally cylindrical but the top surface 185 has a flat axially extending surface and longitudinal grooves that allows room for sutures when the toggle body 180 is in a round delivery tube. The length of the toggle body 180 is substantially longer than the diameter thereof, thus allowing the toggle body 180 to be inserted lengthwise or axially into a small bone hole. Once inserted, unlike most anchors used today, the entire body is pivoted or toggled so that it stays within the bone and has substantially its entire length compressed against material inside the bone. That is, the longitudinal axis of the toggle body 180 is rotated or pivoted from the direction used to insert through the bone hole, thereby preventing its dislodging. This approach means that failure would require the anchor itself to fail, rather than simply it being released (or "pulled out") from surrounding tissue, thus providing improved pullout strength (greater than 600 N before anchor failure when implanted in the array disclosed herein) from an anchor requiring a very small insertion hole (less than about 3 mm). As previously stated, and described in detail below, small insertion holes allow much closer placement of anchors in a high-density array.

The toggle body 180, can have a length of about 6 mm to about 10 mm in some embodiments. This length gives adequate strength while leaving enough room inside the bone for the high number of anchors implanted. The toggle bodies are preferably molded or machined from a polymeric material, preferably a high tensile strength material such as PEEK, which is highly biocompatible. In applications where MRI imaging would not be an issue, metal can be utilized in part or all of the toggle body.

Unlike the toggle body of FIG. 1A, the present toggle body 180 includes two holes through the cross section instead of three. As illustrated, the toggle body 180 has a proximal bore or passage 190 and a distal passage 186. In this embodiment the working suture 195 passes through the distal passage 186 only while the locking suture 198 passes through the proximal passage 190. The passages 186, 190 extend from the top surface 185 to the bottom surface 187 such that the passages 186, 190 extend through the cross section of the elongate body 181. As with the toggle body of FIG. 1A, the present toggle body 180 includes a distal end with an acute angle and a proximal end with projecting fins. These features provide the same aid in assuring toggling during insertion and subsequent tensioning of the anchor as described previously.

Figure 2F:
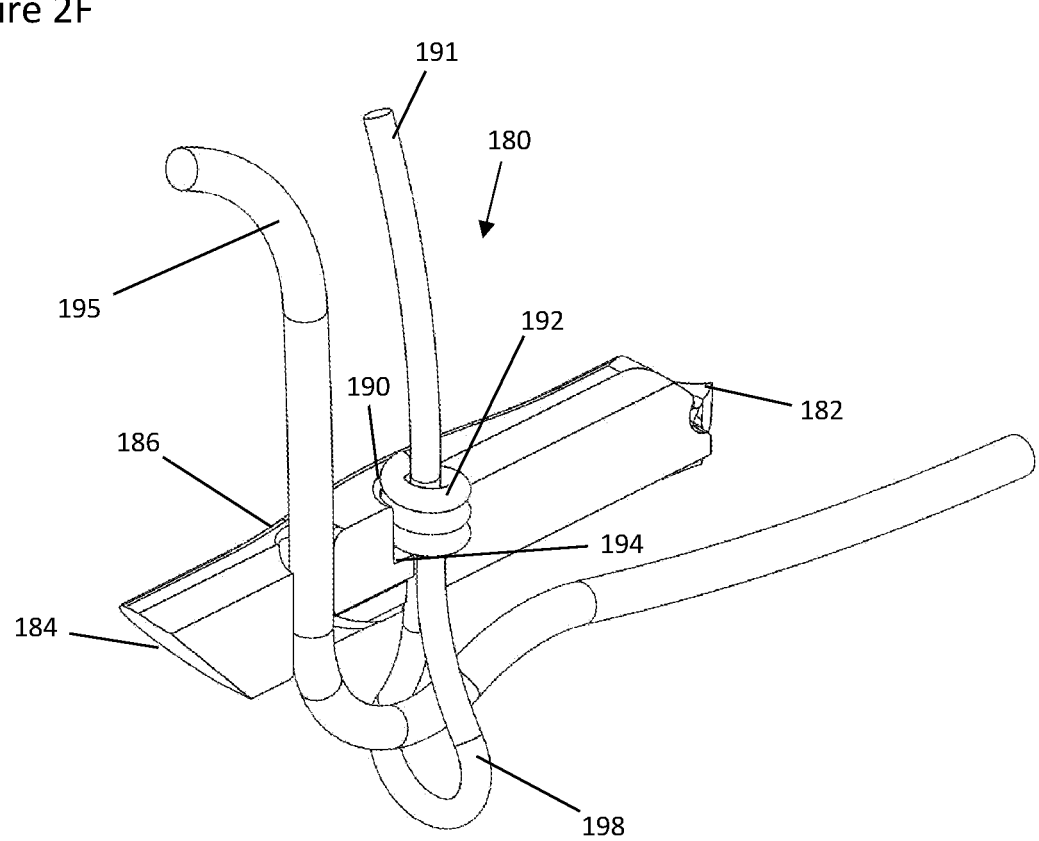
FIG. 2F is a partial cross section of the toggle-body design of FIG. 2E with a working suture and locking loop depicted.

In the illustrated embodiment of FIG. 2E, the distal passage 186 receives a portion of a common working suture 195 therethrough which is slidable with respect to the toggle body 180 during use. This is illustrated in the cross section view of FIG. 2F. The working suture 195 extends into the distal passage 186 from the top surface and extends out at the bottom surface. The working suture 195 can be flossed or is slidable as threaded through the distal passage 186, meaning the toggle body 180 can slide on the suture when tension is applied. Second there is a locking loop 198 that encircles a portion of the working suture 195 as it exits the distal passage 186. The locking loop 198 has a first open position as depicted in FIG. 2F wherein the working suture 195 is free to slide through the locking loop 198 and a second closed position depicted in FIG. 2G wherein the locking loop 198 engages the working suture and prevents it from sliding within the locking loop 198 after the suture is appropriately tensioned. As with previous embodiments, the suture, cord or thread used as working suture or locking suture can be selected from known materials described previously. Also as in previous examples, the free end 191 of the locking loop may have a preferential point of weakness to allow breaking and removal.

Figure 2G:
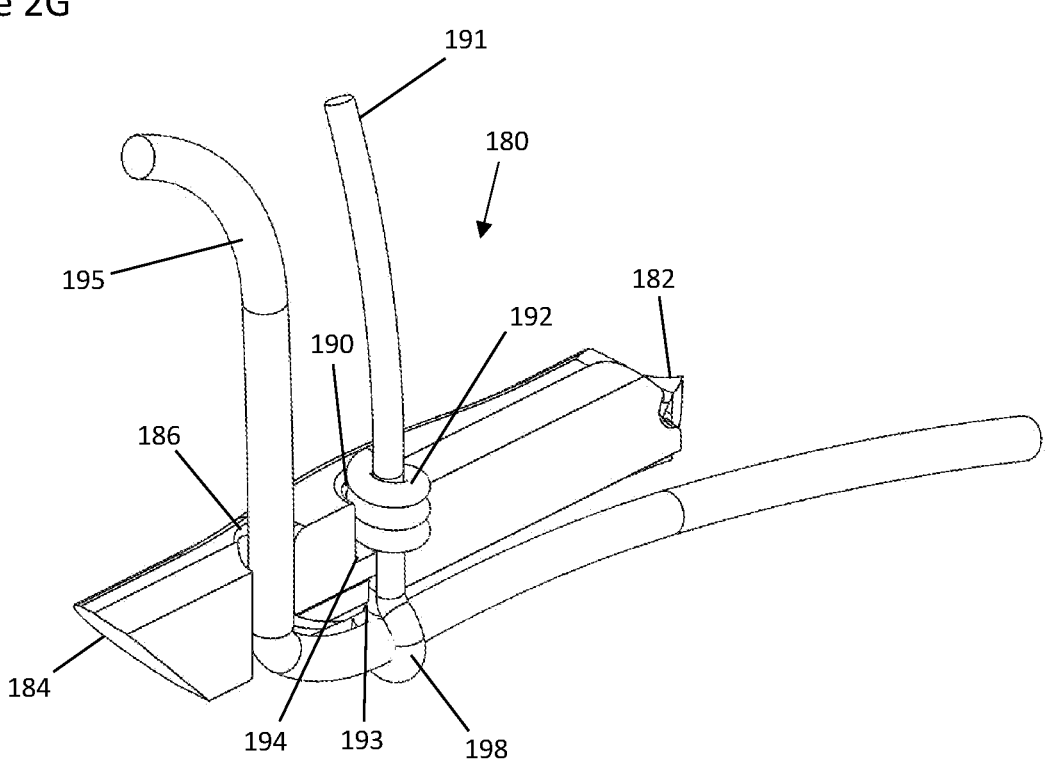
FIG. 2G illustrates the embodiment of FIG. 2F with the locking suture collapsed to lock the suture relative to the toggle body.

This distal passage through which the locking suture extends can be designed to include features described above with respect to the middle passage of FIG. 1A. In particular the locking loop 198, as shown in FIGS. 2F and 2G extends from the bottom surface of the toggle body 180 through the proximal passage 190. The locking loop 198 includes a cord or suture having at least a slidable knot 192 tied therein to allow collapsing of the locking loop 198 when a free end or proximal end 191 of the suture lock 198 extending through the proximal passage 190 is tensioned. As shown, the upper portion of the proximal passage 190 is sized to receive at least a portion of the slidable knot 192 therein. The slidable knot 192 then contacts the surface of the platform 194 which does not allow the knot to pass through towards the bottom opening. The lower oval portion 193 of the proximal passage 190 is a slot or oval (similar to the shape shown in FIG. 1C, at 111) which allows both legs of the locking loop 198 to pass therethrough, preferable side by side in the slot direction. The interaction of these components locks the working suture 195 with respect to the toggle body 180 after the working suture 195 is appropriately tensioned. When the working suture 195 is tensioned, it is pulled up into the bottom opening of the proximal passage which is sized to make the suture less able to floss or move therethrough by increasing frictional resistance to such movement to fully lock the suture. A particularly preferred knot is a 4-throw uni knot. However, other slidable knots 170 may be used, as desired. The working suture 165 is preferably a braided multistrand suture having a compressible cross-sectional area that reduces by at least about 25% when the locking loop is tightened during use. The working suture 165 may be a round No. 2 suture in some embodiments. Other suture types and sizes may be used.

Figure 2H:
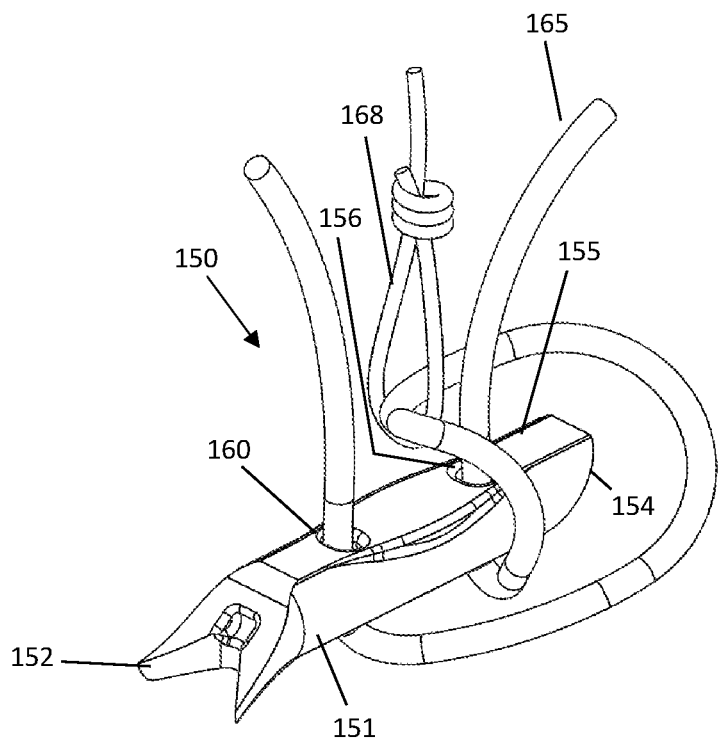
FIG. 2H illustrates a toggle body having a suture routed therethrough to form a one-way locking knot structure.
Figure 2I:
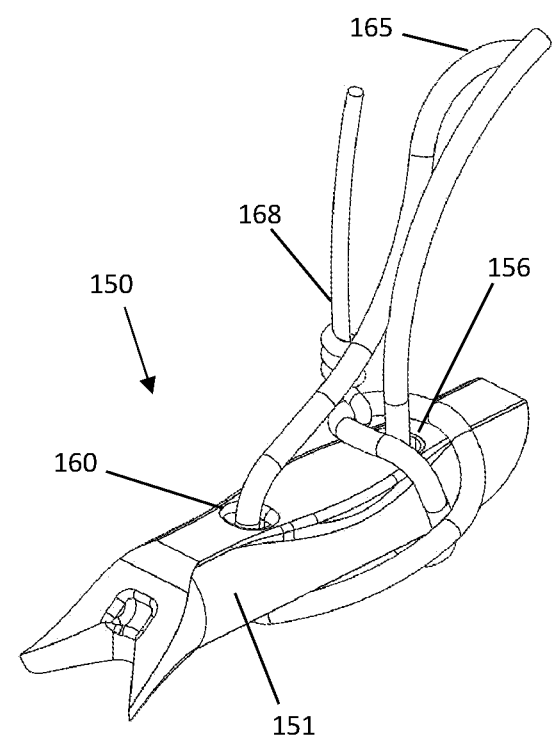
FIG. 2I illustrates the toggle body of FIG. 2H having the locking knot structure in a tensioned position.
Figure 2J:
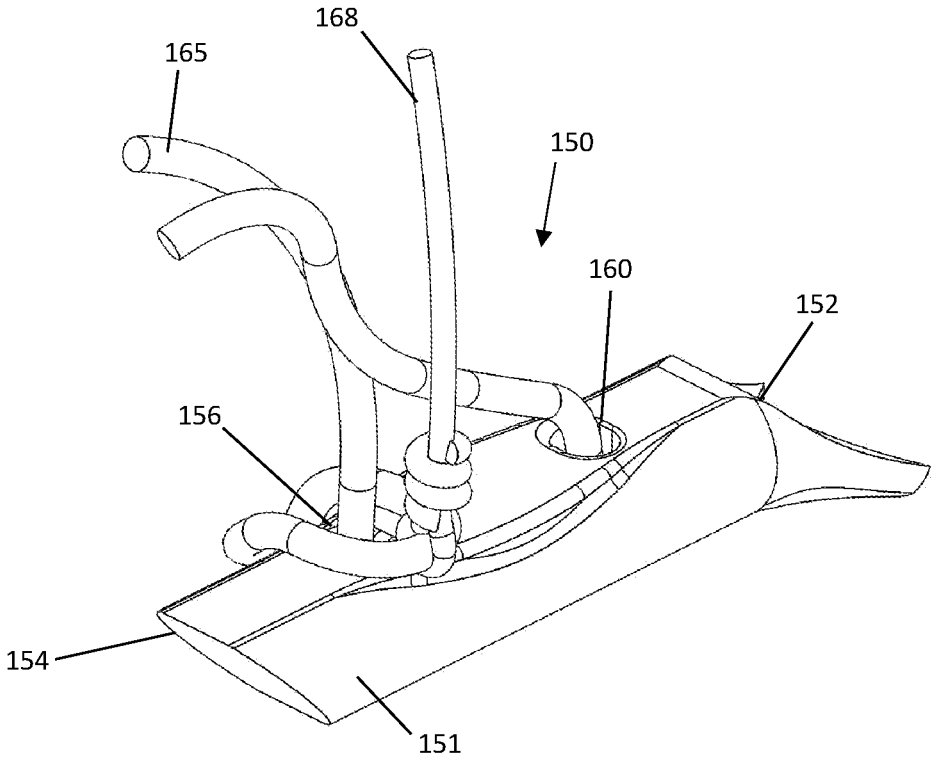
FIG. 2J illustrates the use of a locking loop in conjunction with the locking knot structure of FIGS. 2H and 2I.

Another alternative embodiment of a toggle body and suture arrangement is depicted in FIGS. 2H-2J. As can be seen in the drawings, the toggle body 151 is the same design as the toggle body described above with respect to FIGS. 2A-2D and the individual features are numbered the same. Refer to the description above with respect to FIGS. 2A-2D for features of the toggle body. The difference in this embodiment is the routing of the working suture 165 through the passages 156, 160 to create a one-way knot. The toggle body 151 includes a second hole 160 through the elongated toggle body extending from the first longitudinal surface to the second longitudinal surface at a spaced interval along the elongated toggle body 151 relative to the first hole 156. The working suture 165 exits the first hole at the second longitudinal surface and wraps around the elongated toggle body over the top of the suture extending from the first hole, first longitudinal surface then into the second hole through the first longitudinal surface and out the second longitudinal surface. This forms a one-way locking knot preventing the suture from sliding or increasing friction in one direction but allowing sliding in the other direction. The locking loop 168 can encircle at least one of the overlapping sutures proximate their intersection. Alternatively, the locking loop 168 can encircle both of the overlapping suture portions proximate their intersection. The free end of the suture attached to the locking loop 168 may, as in other examples, include a preferential point of weakness allowing breaking and removal thereof, if desired.

Figure 2K:
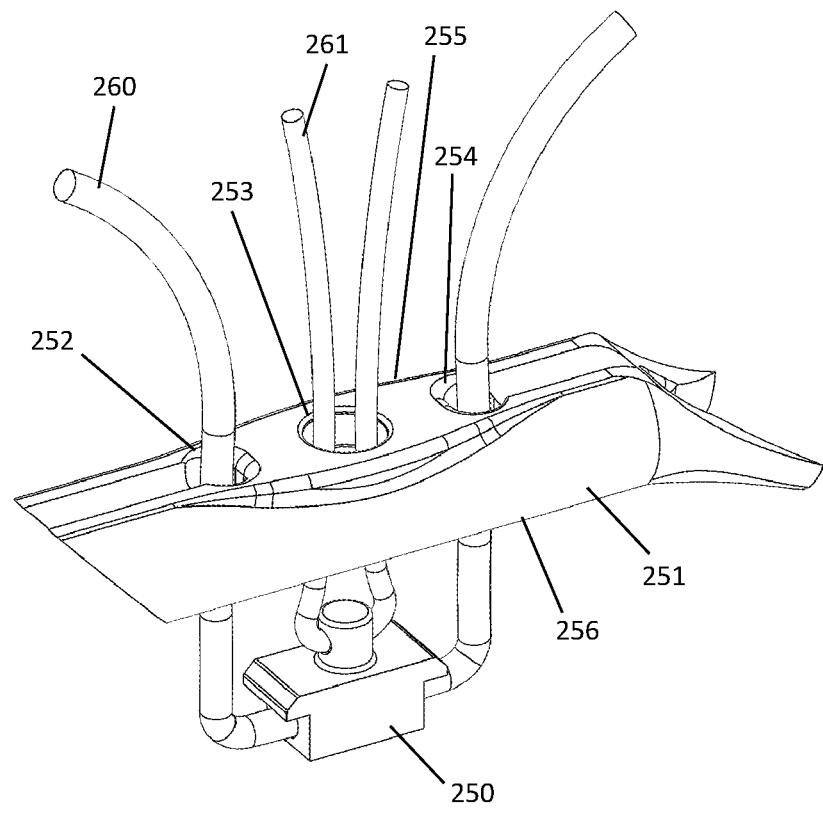
FIG. 2K is a perspective view of an alternative toggle-body design including a suture locking member.
Figure 2L:
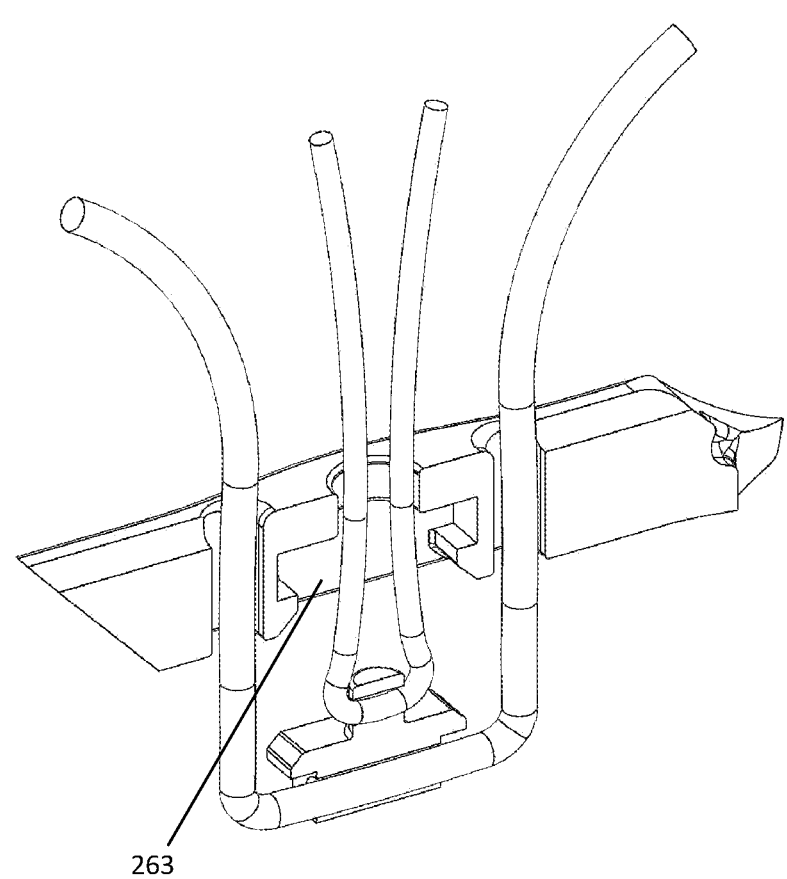
FIG. 2L is a cross section view of the design of FIG. 2K illustrating the functioning of the locking member.

Alternatives to the locking loop described with respect to previous embodiments can also be included in some designs. Referring to FIGS. 2K-2L, one embodiment incorporating a locking member 250 is depicted. The toggle body 251 is very similar in design as the toggle body of FIG. 1A. As illustrated, the toggle body 251 has a proximal bore or passage 254, a middle passage 253 and a distal passage 252. The passages extend from the top surface 255 to the bottom surface 256 such that the passages extend through the cross section of the elongate body. In other embodiments, the toggle body may have fewer or more bores or passages, such as having a single bore, two bores, or more than three bores. In the illustrated embodiment, the proximal passage 254 and distal passage 252 receive a portion of a common working suture 260 slidable with respect to the toggle body 251 during use. The middle passage 253 receives a locking member 250 and associated pull suture 261 which is independent for each anchor used in an array of anchors.

In this embodiment the locking member 260 is included which at least partially encircles the working suture 260 proximate the second longitudinal surface 256 adjacent the elongated toggle body 251. The locking member is moveable between a first position allowing the suture to slide through the locking member and a second position preventing the suture from sliding through the locking member in at least one direction. The locking member can be slidably received in a chamber formed in the elongated toggle body (depicted in cross section in FIG. 2L) and in the first position has a portion spaced radially from the longitudinal surface to allow suture movement while in the second position the locking member is held deeper within the chamber and creates a pinched tortuous pathway for the suture to prevent suture movement. In the embodiment shown, the locking member includes a snap fit within the chamber when the locking member is moved to the second position.

As with some other embodiments, the toggle body 251 can include a third hole 253 through the toggle body extending from the first longitudinal surface to the second longitudinal surface and located between the first and second holes, wherein the locking member further comprises a pull suture 261 extending from the locking member through the third hole at the first longitudinal surface after passing through the toggle body. As illustrated in the section view of FIG. 2L, the toggle body 253 can include a cavity 263 for receiving the locking member 250 therein. By pulling on the pull suture 261, the locking member 250 would be drawn up into the cavity 263, such that the working suture 260 will have to traverse a tortuous path on the bottom side of the toggle body 251. For example the locking member 250 may snap into place in the cavity 263. The pull suture 261, if dispositioned as shown, may simply be released at one end and removed entirely from the toggle body structure. Alternatively, the pull suture 261 may be secured, as by a knot, onto the locking member 250 and may include a preferential point of weakness (as previously discussed, above) allowing the free end thereof to be broken and removed.

Figure 3A:
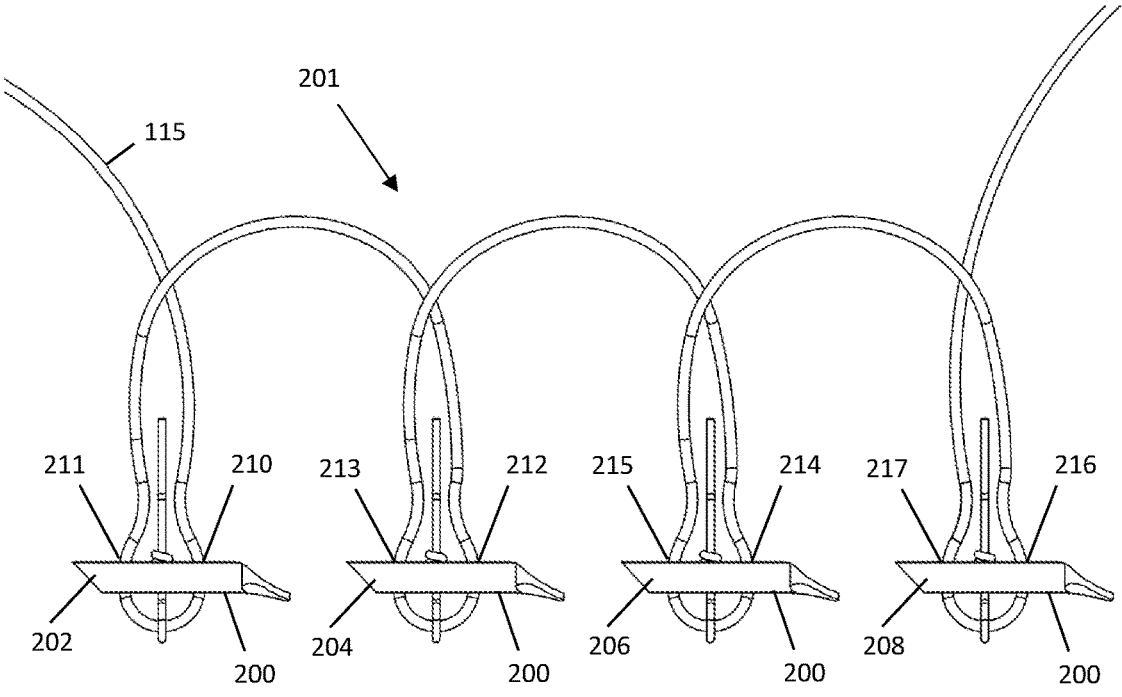
FIG. 3A is an illustration of a pre-threaded array of toggle type anchors.

In some preferred embodiments, the above described anchors do not function alone. Instead each may be a part of a pre-strung array of anchors having a common serially disposed working suture 115 therethrough. FIG. 3A illustrates a pre-strung array 201. The array is depicted and described with respect to the anchors of FIGS. 1A through 1J but is equally applicable to the anchors of FIGS. 2A through 2L. Each anchor 200 can be implanted sequentially within the array, then the working suture section extending from the just implanted anchor to the previously implanted anchor can be tensioned, then locked at the just implanted anchor so that a suture stitch between the two anchors provides force against the tendon to hold it in place much like a single sewn stitch. With the array, multiple continuous stitches can be formed similar to a sewn seam.

In FIG. 3A a pre-strung array 201 of individual anchors 200 is depicted. The anchors 200 may be similar in form and function to the any of the anchors described herein. The shown array has four anchors 200 as a representative chain. It is believed chains of as few as 4 and as many as 12 anchors would be useful in tendon repair procedures such as rotator cuff repair depending on tear characteristics and surgeon preferences. One particular embodiment includes 8 anchors in an array. As depicted in FIG. 3A, the way in which the working suture 115 is pre-threaded through the series of anchors 200 is important to assure that they will toggle as desired and tension to form the secure stitch when the suture is tightened. The illustration shows the first anchor 202 to be implanted followed by the second anchor 204, then the third anchor 206 and finally the fourth anchor 208. With this order of implantation understood, the working suture 115 has been pre-threaded down through the top of the proximal hole 210 and back up through the distal hole 211 of the first anchor 202. The working suture 115 then continues to the second anchor 204 where it is threaded down through the proximal hole 212 and back up through the distal hole 213 of the second anchor 204. The working suture 115 then continues to the third anchor 206 where it enters the top of the proximal hole 214 and back up the distal hole 215 of the third anchor 206. The working suture then continues to the fourth anchor 208 where it enters the top of the proximal hole 216 and passes up through the bottom of distal hole 217 of the fourth anchor 208. If the array were more than four anchors, the pre-threading would continue as described for each subsequent anchor.

Figure 3B:
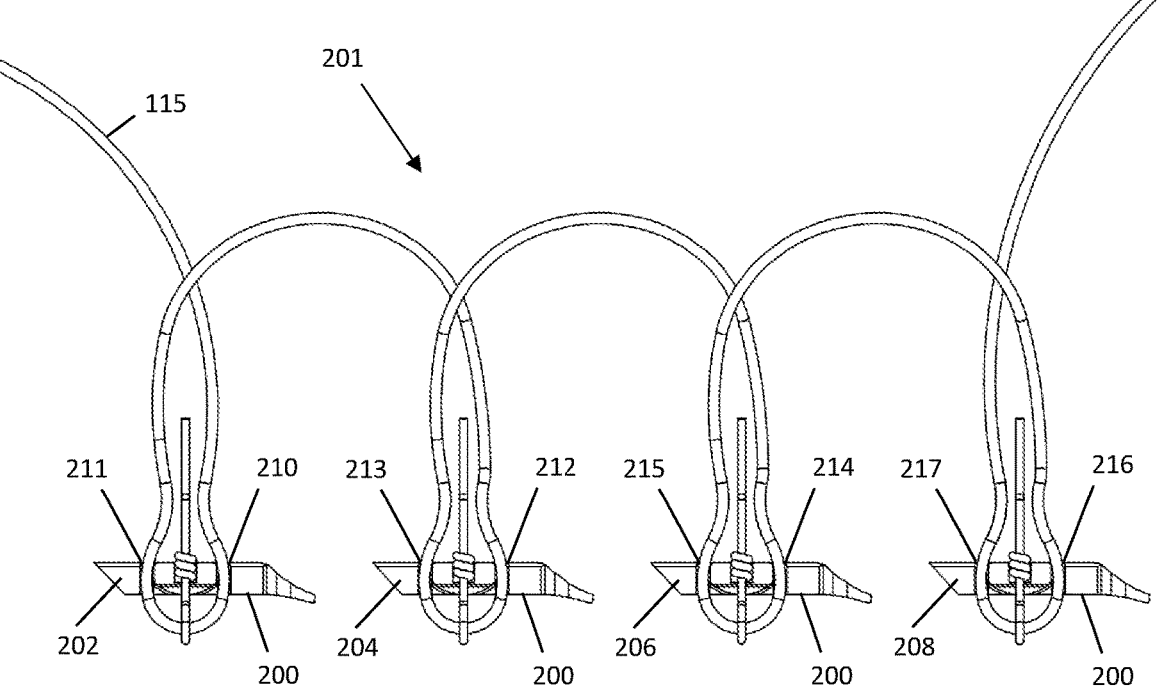
FIG. 3B is an alternative view of FIG. 3A showing the toggle anchors in cross section to illustrate the threading route of the sutures.

FIG. 3B is a cross sectional view of the array of FIG. 3A which more clearly shows the threading of the working suture 115 within the anchors 200 in the array 201. The way in which the locking suture 116 is disposed in the middle passage is also shown for each anchor 200 as described above with each locking loop 118 independent for each anchor. The locking suture 116 can have a preferential point of failure so that it can be tightened then purposefully broken off above the slidable knot. This can be accomplished by tying a knot in the free tail of the locking loop just above the slidable knot. In some preferred embodiments the slidable knot is a 4-throw uni knot and the knot are in the free tail just above the uni knot. The suture is selected to break at a desired tension with the knot in place sufficient to lock the working suture. Tying of each knot may be performed as part of the assembly and/or manufacturing of the anchors, rather than being a task for the implanting physician, who may instead complete implantation without having to tie knots associated with placement of the anchors. It will be recognized that for other examples shown above, the locking suture 116 may be differently disposed, or may instead couple to a locking member.

To create an implanted serial array of tensioned and independently locked anchor to anchor suture stitches for attaching a tendon to bone, a surgeon would begin with the pre-strung array 201 described in FIGS. 3A and 3B. The first anchor 202 would be implanted through the tendon into a formed bone hole and the working suture locked. The first anchor can include a tied suture that does not floss or it can include an anchor that has a locking loop that is pre-locked before implant or after implant as desired. The second anchor 204 would then be implanted in close proximity to the first anchor 202, preferably less than 7 mm away (less than or equal to about 10 mm center of hole to center of hole). The second anchor is toggled and the working suture tensioned at the same time by pulling on the working suture 115 that exits the distal hole 213 of the second anchor 204. Tension at this location not only toggles the second anchor 204 but also tightens the working suture 115 going back to the first anchor 202 to form the tensioned stitch securely reapproximating the tendon against the footprint. The second anchor 204 is then locked using a suture lock, locking suture or locking member as described previously, so that the stitch remains tensioned and is isolated or independent of other stitches. The process is repeated for the third anchor 206 and fourth anchor 208 or more. In one preferred array, eight anchors are implanted and 7 tensioned and locked stitches in a continuous row are formed. Further, in a rotator cuff repair, multiple arrays can be implanted such as one array extending across the tendon in the medial portion of the footprint and a second array more lateral to the medial position.

Figure 4A:
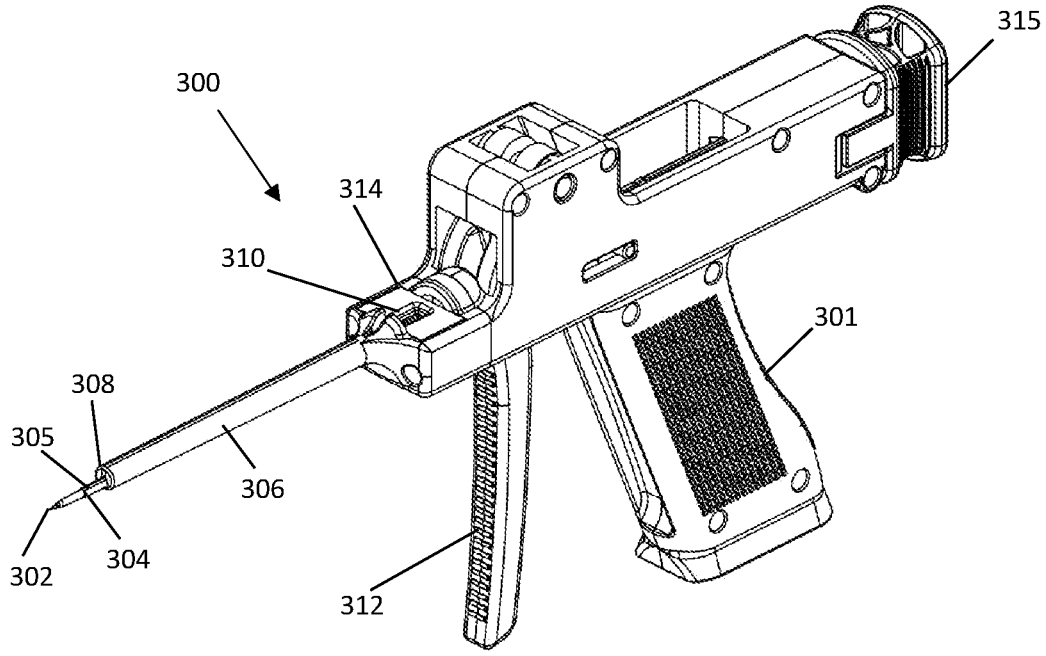
FIG. 4A is a perspective view of an example anchor delivery device.

One anchor delivery device 300 for transtendinous implantation of individual anchors in an array is depicted in FIG. 4A. The delivery device 300 includes a handle assembly 301 having an outer tubular shaft 306 affixed thereto and extending distally therefrom. The outer tubular shaft 306 has a lumen extending through it. An anchor delivery tube 308 extends through the lumen of the outer tubular shaft 306 having a proximal end affixed to the handle assembly 301. The distal end of the anchor delivery tube 308 terminates distally at the same location as the outer tubular shaft 306. The distal end of the outer tubular shaft 306 along with the distal end of the anchor delivery tube 308 provide a surface that abuts the tendon when the anchor delivery device 300 is in position. It provides a bearing face that presses against the tendon and underlying bone which also counters the opposite force applied when the anchor is pulled into position. This reduces the chance of any anchor dislodging or pullout if being placed in relatively soft or fragile bone of a particular patient.

A spring-loaded nub assembly 304 having a distal nub portion extends within the anchor delivery tube 308 and has a distal nub portion 305 extending a distance distal of the anchor delivery tube 308. The distal nub portion 305 can be retractable within the anchor delivery tube 308 when force is applied to the distal end of the nub assembly. If desired, an anchor delivery tool having a handle adapted to apply a positive retraction force to the nub portion 305 may be used, as shown in U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TIS-SUE TO BONE, the disclosure of which is incorporated herein by reference.

Figure 4B:
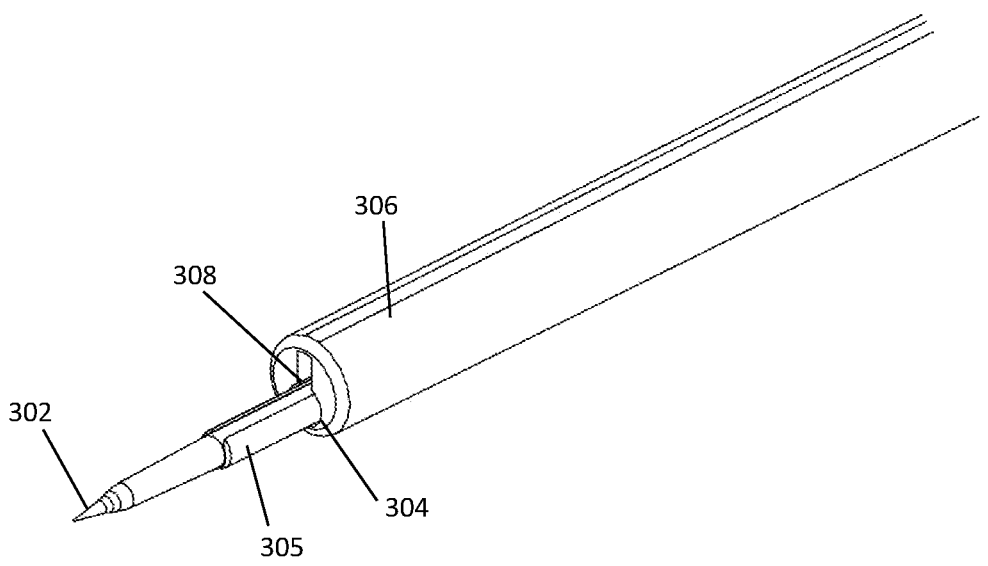
FIG. 4B is a close up view of the distal end of the anchor delivery device of FIG. 4A showing the outer tube, delivery tube, nub and bone punch relationship.

A bone punch assembly 302 extends through the lumen of the anchor delivery tube 308 and the distal nub portion 305 with a pointed distal end terminating a distance distal of the distal end of the distal nub portion 305, wherein when fully inserted, a shoulder 314 on the bone punch assembly near the proximal end of the nub assembly blocks proximal movement or retraction of the nub portion 305, locking it in an extended position for insertion through the tendon into bone. The close-up view of the distal portion of the delivery device in FIG. 4B better shows the relationship of the outer tubular member 306, the anchor delivery tube 308, the nub assembly 304, distal nub portion 305, and bone punch 302. As can be seen, the distal end of the bone punch 302 extends beyond the distal nub portion 305 when fully extended for use in implantation.

Figure 4C:
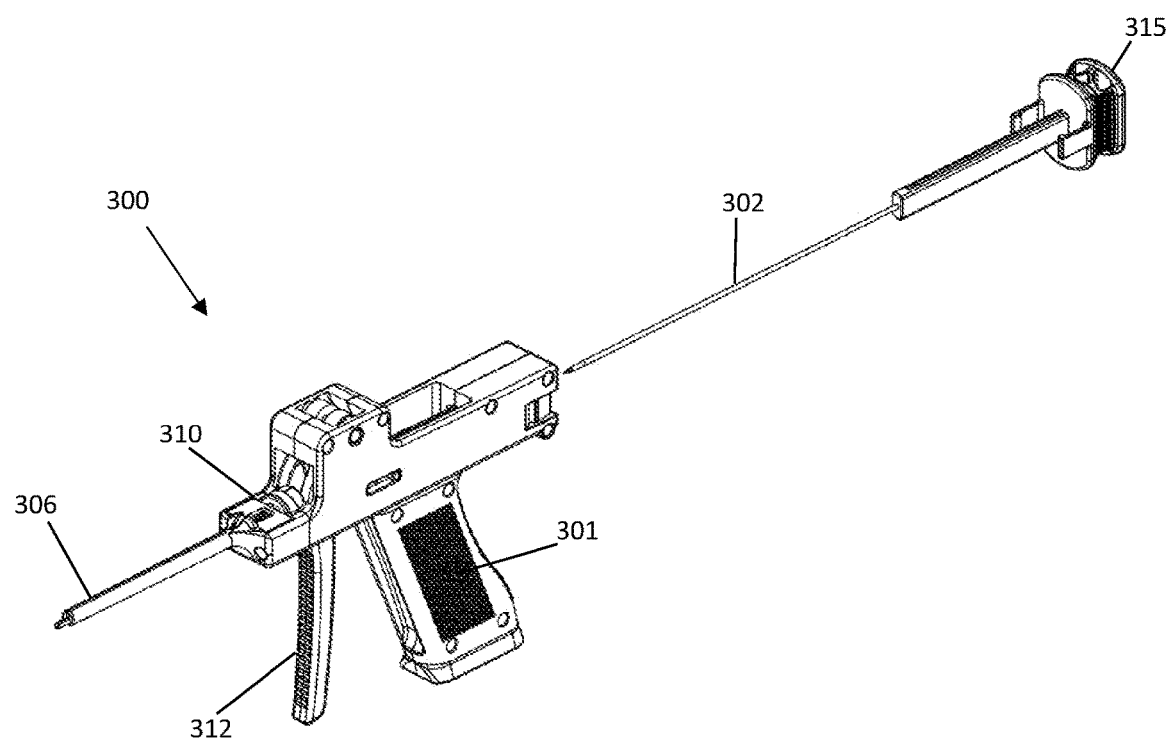
FIG. 4C is a perspective view of the delivery device of FIG. 4A with the bone punch retracted.

In some embodiments the anchor delivery tube 308 can include a longitudinal slot over its length to allow passage of sutures therethrough into the lumen of the outer tubular shaft 306. The outer tubular shaft 306 can preferably include a solid wall over its length. The delivery device also can include an anchor loading chamber 310 in communication with the proximal end of the anchor delivery tube 308 for receiving a toggle-type anchor therein. With this embodi-ment the bone punch assembly 302 blocks the anchor loading chamber 310 when fully inserted and allows access to the chamber 310 when retracted. A delivery device with the bone punch assembly 302 retracted is shown in FIG. 4C. The bone punch assembly 302 has a proximal end extending from the delivery device with a flat surface 315 for pounding the extended punch into bone. Additionally, a trigger lever 312 is included on the delivery device that is connected via a linkage to the bone punch. When the trigger is pulled the linkage applies a retracting force to the bone punch assem-bly 302 to pull the punch from bone.

Figure 4D:
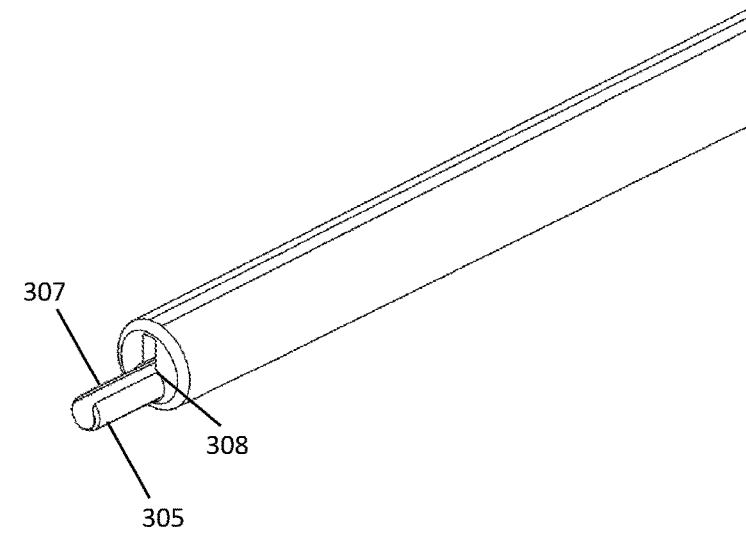
FIG. 4D is a closer view of the distal end of the delivery device of FIG. 4C showing the outer tube, delivery tube and nub relationship with the bone punch retracted.

Now referring to FIG. 4D, the distal end of the delivery device is shown with the bone punch retracted. As can be seen in the image, the distal nub portion 305 extends beyond the distal end of the anchor delivery tube 308 and outer tubular shaft 306. The distal nub portion 305 also includes a longitudinal slit 307 for passing a suture therethrough. The distal nub portion 305 can be semi-circular and may con-form to the outer surface of the punch pin. It can have a thickness of about 0.0075 inches (0.19 mm) or less. With the bone punch retracted, the distal nub portion 305 is now able to move proximally into the anchor delivery tube 308 if a force is applied to the distal end of the nub assembly 304. This can be important as the distal nub portion 305 is extended during the toggling of an anchor which might contact the distal nub portion 305 when the anchor is pulled into place. With this embodiment the distal nub portion 305 simply pushes into the anchor delivery tube 308 and does not interfere with anchor toggling.

Figure 4E:
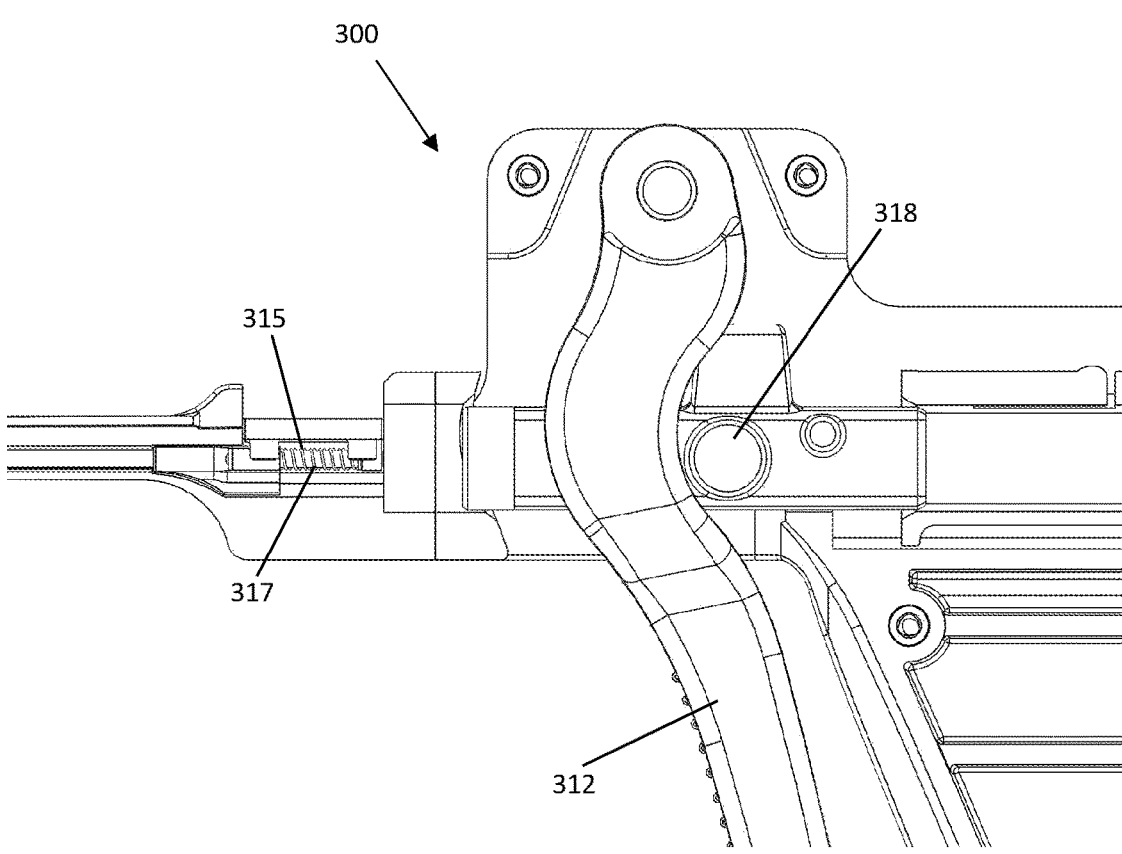
FIG. 4E is cross section view of the delivery device of FIG. 4A illustrating the mechanism to assist withdrawing the bone punch from bone and the unlocking of the nub.

More detail of the functioning of the delivery device is provided in FIG. 4E, which depicts a partial cross section view of the delivery device 300 in the portion that includes both the trigger mechanism and the proximal spring-loaded portion of the nub assembly. The pulled trigger 312 engages the punch pin boss 318 to move the entire punch pin assembly 302 proximally. When pulled proximally, the shoulder that held the proximal end of the nub assembly in a fixed position is also moved proximally. This frees the proximal end of the nub assembly 315 to move proximally against the resistive and restorative force of the spring 315. As describe above, the assembly allow the distal nub portion 305 to retract into the anchor delivery tube 308 if the anchor contacts the distal nub during toggling and moving into final position.

Some examples may use an anchor delivery tool as shown in U.S. Prov. Pat. App. No. 63/281,411, filed Nov. 19, 2021, titled DELIVERY DEVICE FOR IMPLANTING KNOT-LESS MICRO-SUTURE ANCHORS AND ANCHOR ARRAYS FOR ATTACHMENT OF SOFT TISSUE TO BONE, the disclosure of which is incorporated herein by reference. Some features of such an anchor delivery tool relevant to the above discussion may include a proximal assembly that controls the extension and retraction of the nub depending on the stage of implantation. For example, a trigger may be provided such that when the bone punch is first extended to its fullest extent, pulling the trigger causes the bone punch to be retracted, while the nub is held in an extended position, registering the nub with the created bone hole.

When the bone punch is again extended fully to insert the anchor, the trigger changes configuration so that a second pulling or actuation of the trigger forces retraction of both the bone punch and the nub into the distal end of the anchor delivery tube 308, moving the nub out of the bone hole to prevent interference with or damage to the working suture and/or suture anchor free end as the anchor is toggled into position, and also as the working suture is tensioned and locked. In addition, an anchor delivery tool as shown in the 63/281,411 Provisional Application may include a plunger assembly to controllably insert a cartridge carrying an anchor into position for advancing down the anchor delivery tube, where the positioning of the plunger also controls whether the trigger is adapted to retract only the bone punch, or is adapted to retract both the bone punch and the nub. A range of other design features are also disclosed in the 63/281,411 Provisional Application that may also be used in association with the alternative anchors, working suture configurations, and locking features disclosed herein.

Figure 4F:
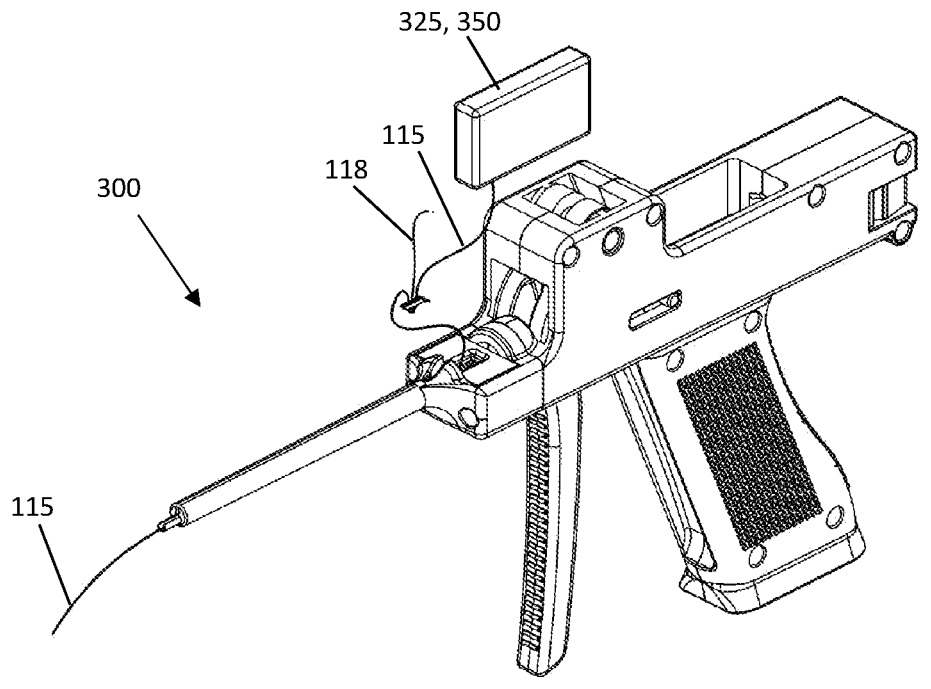
FIG. 4F is a perspective view of the delivery device of FIG. 4A and an exemplary toggle anchor cartridge.
Figure 4G:
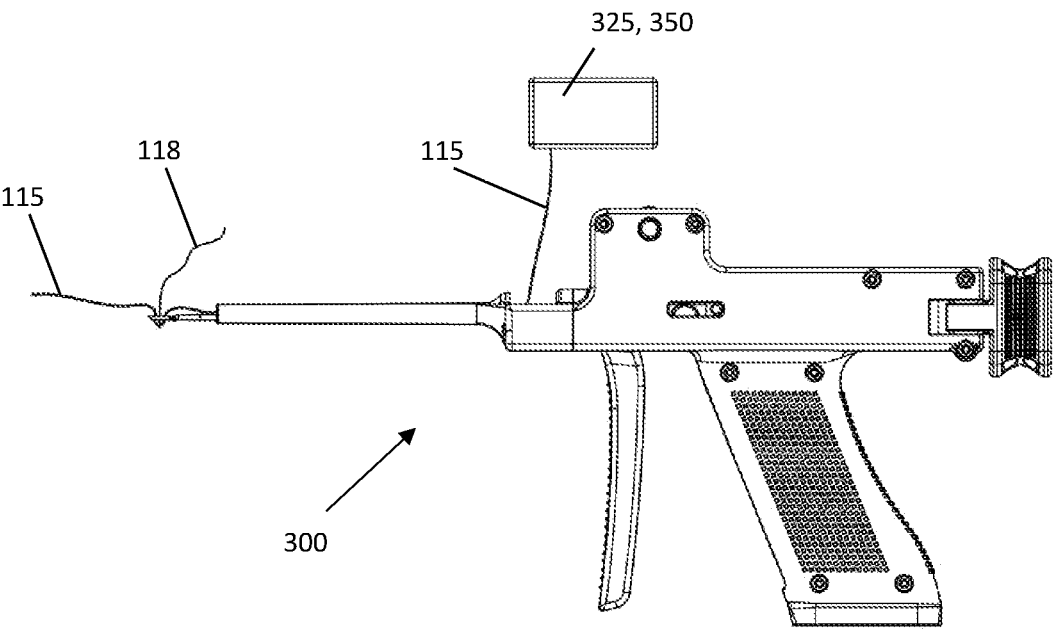
FIG. 4G illustrates a toggle anchor as it is delivered to the distal end of the delivery device.
Figure 4H:
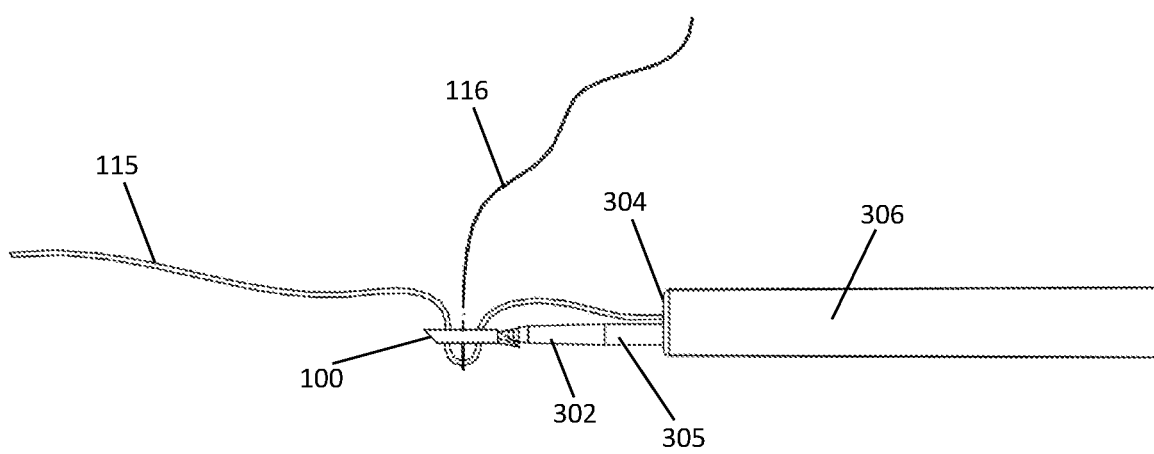
FIG. 4H is a closer view of the distal end of the delivery device and toggle anchor of FIG. 4G.

In order to use the above delivery device with an array of pre-strung toggle type anchors, certain embodiments include an anchor cartridge which is made up of individual anchor holders having suture management features. This is shown schematically in FIGS. 4F and 4G. For example, the array of FIG. 3A would have a cartridge 325, 350 with four indi-vidual holders 326. Referring to FIGS. 4F, 4G and 4H, it can be seen that the cartridge is depicted with an anchor removed from the cartridge and holder. This shows the way in which the working suture 115 remains threaded through both the anchor still in the cartridge and the anchor that has been removed from the cartridge. Also, the working suture on all anchors except the first anchor inserted will extend through the delivery device and out the distal end to maintain the continuous string of anchors. FIG. 4F shows the anchor prior to loading into the delivery device. In contrast, FIG. 4G and the closer view of FIG. 4H, show the anchor as it would emerge from the distal end of the delivery device upon being pushed with the punch pin. As detailed below, the distal end would be positioned in bone of the humeral head before the anchor is implanted but shown here outside the body to understand the concept of managing the continuous thread of working suture in the array of anchors.

An exemplary holder design 326 is depicted in FIGS. 5A-5D. In some preferred embodiments, the holder 326 has a casing 327 with an open volume 328 therein for slidably disposing one of the toggle bodies 100. As shown in FIG. 5A-5D, the holder 326 can include a plurality of arms that are positioned to extend into the open volume 328 to support and releasably hold the toggle body 100 in a fixed position. The holder 326 can include a raised boss 332 having a cylindrical surface 333 spaced below the inserted toggle body with side surfaces in alignment with the proximal 110 and distal 106 passages of the toggle body 100.

Figure 5A:
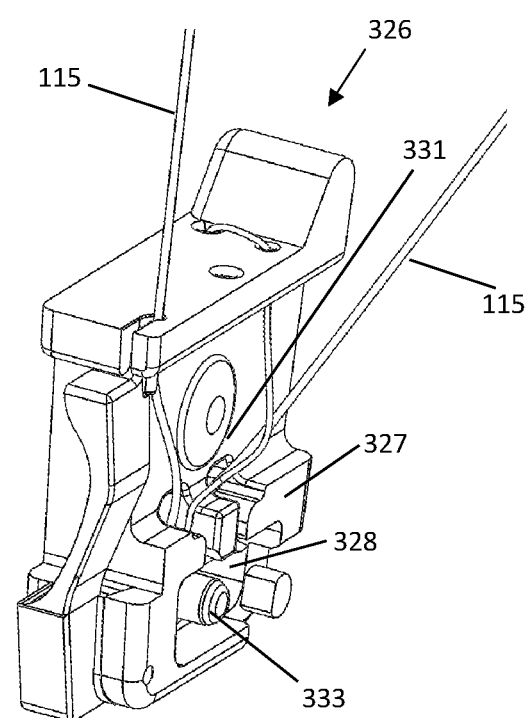
FIG. 5A is a first side view of a toggle anchor holder embodiment.
Figure 5B:
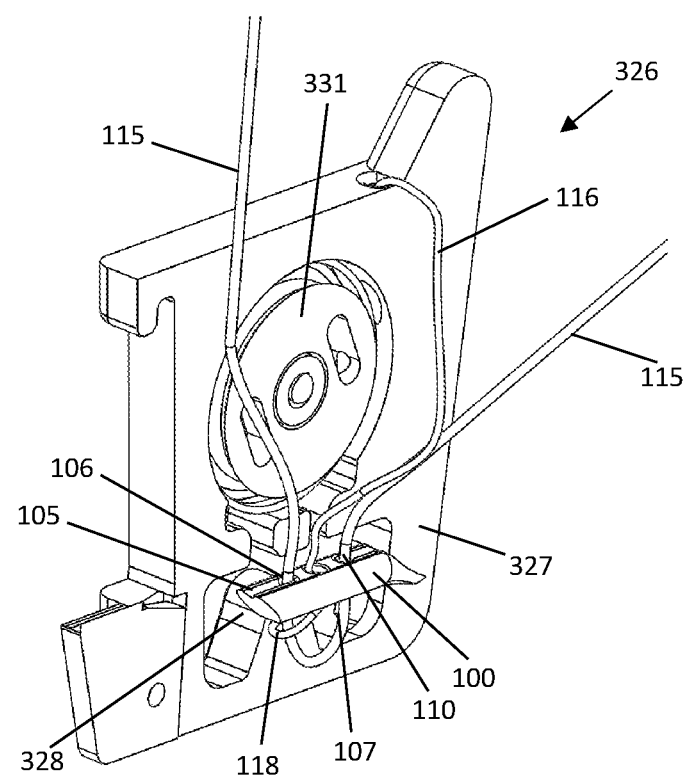
FIG. 5B is a partial section view of the toggle anchor holder of FIG. 5A showing the position of the toggle body and suture management features.
Figure 5C:
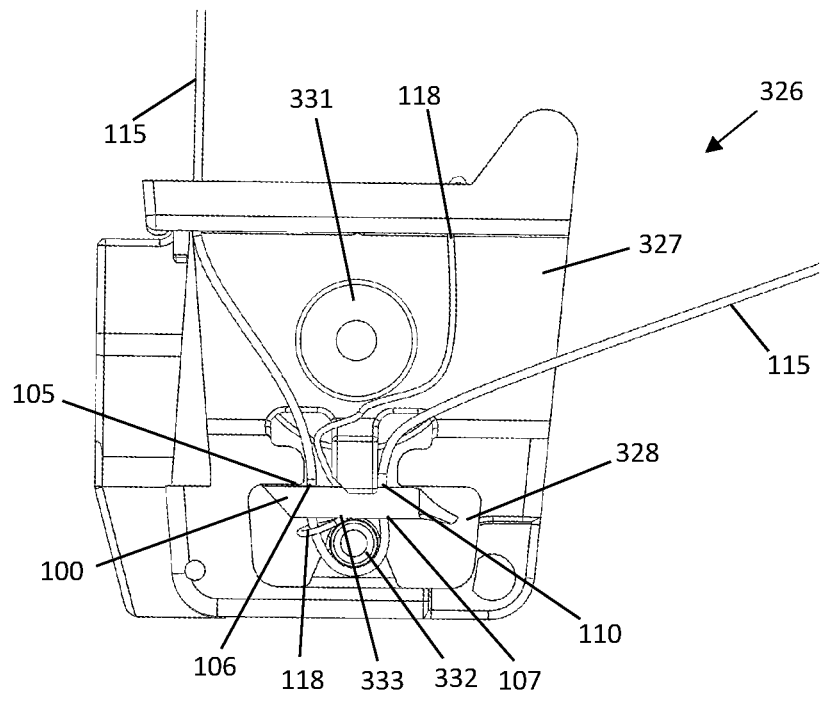
FIG. 5C is a second side view opposite the first side view of the toggle anchor holder of FIG. 5A.
Figure 5D:
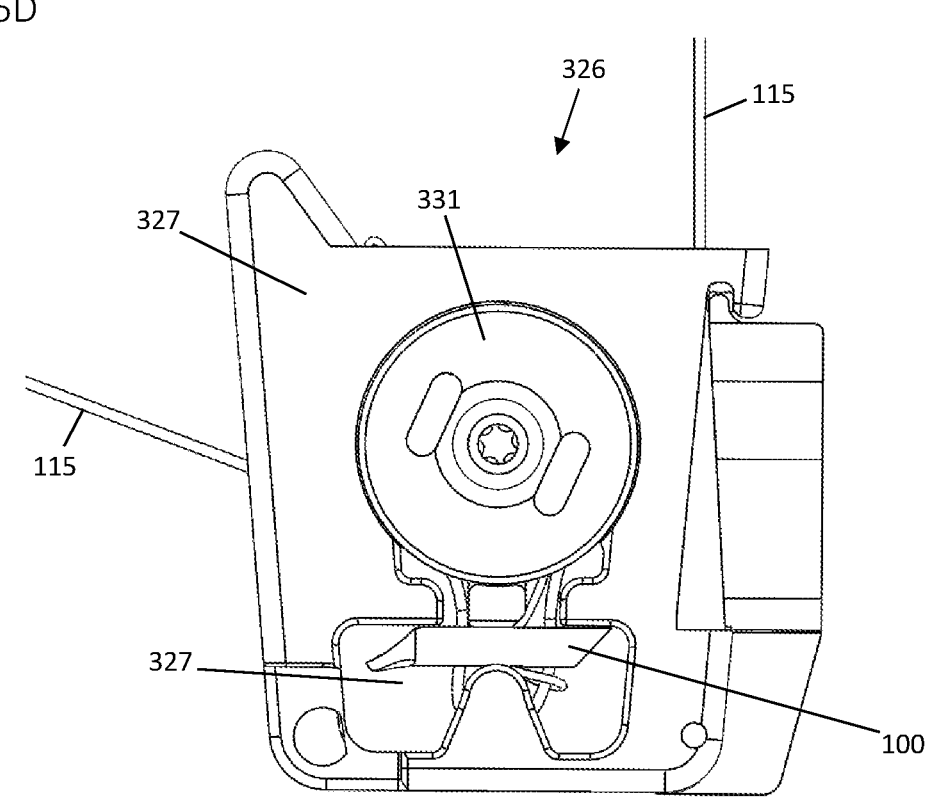
FIG. 5D is a top perspective view of the toggle anchor holder of FIG. 5A.

As with the array of FIG. 3A, a single working suture 115 serially connects the plurality of toggle bodies as positioned in each holder. FIG. 5B shows the single working suture 115 passes into a side of the casing 327 in alignment with and then passing through the proximal passage 110 at the top surface and out at the bottom surface 107 of the toggle body 100, around the cylindrical surface 333 of the boss 332 (see FIG. 5C), then back up through the distal passage 106 at the bottom surface out the top surface 105 of the toggle body 100, and exiting the top portion of the casing 327 in alignment with the distal passage top surface of each toggle body. Within each holder 326 is the independent locking loop 118 for each toggle body 100. As placed in the holder 326, the locking loop 118 extends from the middle passage 108 at the bottom surface 107 and encircles a portion of the section 117 of the working suture 115 proximate the boss 332, the locking loop 118 having a first open position allowing the working suture 115 to slide through the locking loop 118 and a second closed position engaging the working suture 115 and preventing sliding of the working suture 115 within the locking loop 118 after implantation. The holder 326 can include a spool 331, as depicted in FIG. 5D, around which the tightening leg of the locking suture 116 is wrapped until used. The exemplary cartridge design features are shown with the anchor of FIGS. 1A-1K, but with minor modifications for suture routing are equally applicable to alternative anchor designs depicted in FIGS. 2A-2L.

Further alternative designs for cartridges and magazines of cartridges that may be used in other examples are disclosed in U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference. For example, the cartridge may comprise a moving or sliding cover that holds the suture anchor in a desired position securely until the cartridge engages with or is inserted into a slot of the anchor delivery tool. The cartridge may be designed to allow release of the anchor in a lateral direction or in an axial direction, as disclosed further in the 63/281,411 Provisional Application.

In FIGS. 6A through 6G, an exemplary method for implanting both individual anchors and an array of anchors is depicted. Further, FIGS. 6H and 6I illustrate an example of suture stitch arrays as implanted on the surface of a rotator cuff tendon having anchor to anchor continuous stitches that are independently tensioned and locked that can result from using this technology.

Figure 6A:
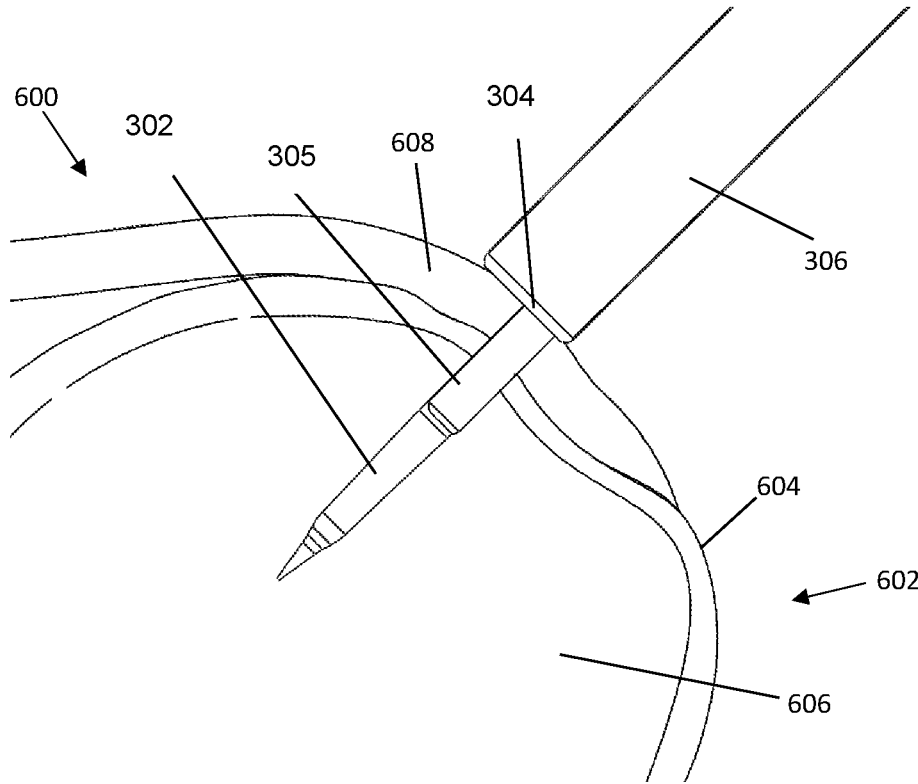
FIGS. 6A-6I illustrate the steps for implanting exemplary anchors of the current invention and resulting pattern of continuous tensioned and locked anchor to anchor single suture stitches.

Referring first to FIG. 6A, a schematic of select parts of the shoulder rotator cuff 600 is depicted in order to explain the methods of implantation. The illustration includes a portion of the humeral head 602 shown including an outer cortical shell layer 604 and an inner cancellous bone material 606. A tendon, in this case the supraspinatus tendon 608 is shown overlaying a portion of the humeral head where it is to be attached to the footprint. The method is a transtendinous or through-the-tendon repair.

The tendon 608 is first positioned in a desired location for reattachment to bone on the footprint of original attachment. The delivery device of FIGS. 4A-4G, or similar (such as in U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference), is then utilized to implant the toggle type suture anchor through the tendon 608. To begin the delivery device is set as in FIG. 4C with the distal nub 305 extending from the distal end of the implant delivery tube 304 and elongate tube 306. The bone punch 302 is fully inserted distally so that it extends beyond the distal end of the nub 305 and is locked in place, as is the nub locked in place. The device as configured is positioned on the tendon at the desired anchor placement and pounded in until the distal end of the elongate tube 306 is in contact with the tendon as shown in FIG. 6A. At this point the nub 305 extends through at least a portion of the cortical shell 604 (in thinner bone the nub 305 can extend into the cancellous bone 606) and the distal end of the bone punch 302 extends deeper into the cancellous bone 606. To achieve the desired depth of implantation to assure toggling, the bone punch extends beyond the outer tube distal end a distance of greater than or equal to about 20 mm. Further, to assure nub registration with the bone hole, the nub portion 305 extends beyond the outer tube 306 distal end a distance of about 6 to about 10 mm.

Figure 6B:
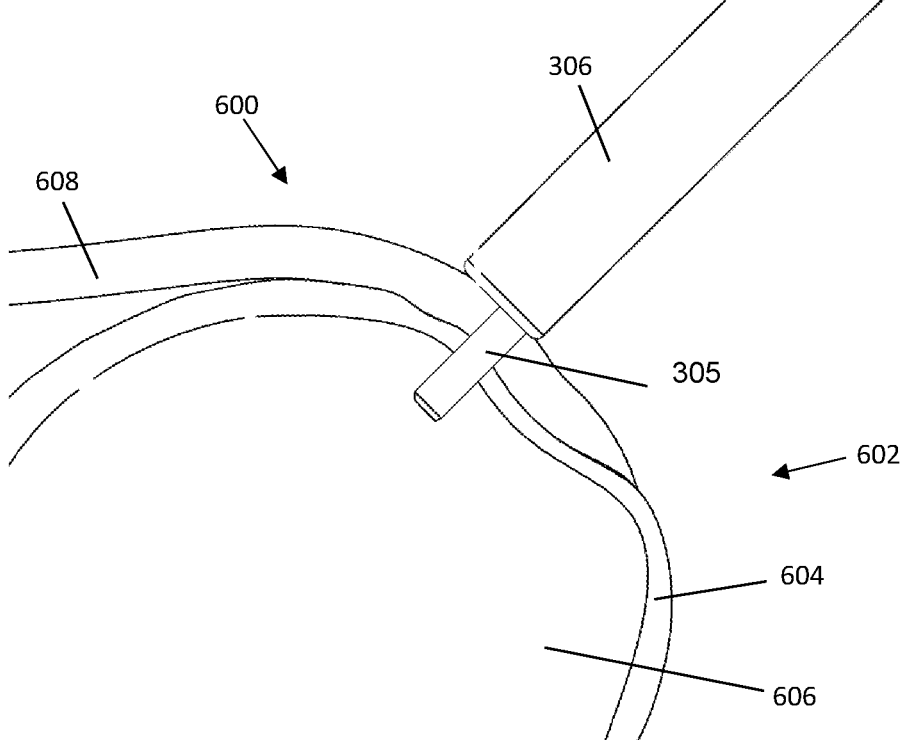

As depicted in FIG. 6B, the bone punch 302 is then retracted while maintaining the anchor delivery tube 304 and nub portion 305 in place, with the nub portion 305 providing registration with the formed hole in the bone. Absent such registration with the bone hole by the nub portion 305, the location under the tendon would be lost and it would be very difficult to feed an anchor through the tendon which would tend to fill the hole through which the bone punch traveled. In some examples, this step of the method may be performed by depressing a trigger on an implant tool where the implant tool is configured to maintain the nub portion 305 extended in certain configurations while applying a positive retraction force to the bone punch 302.

Figure 6C:
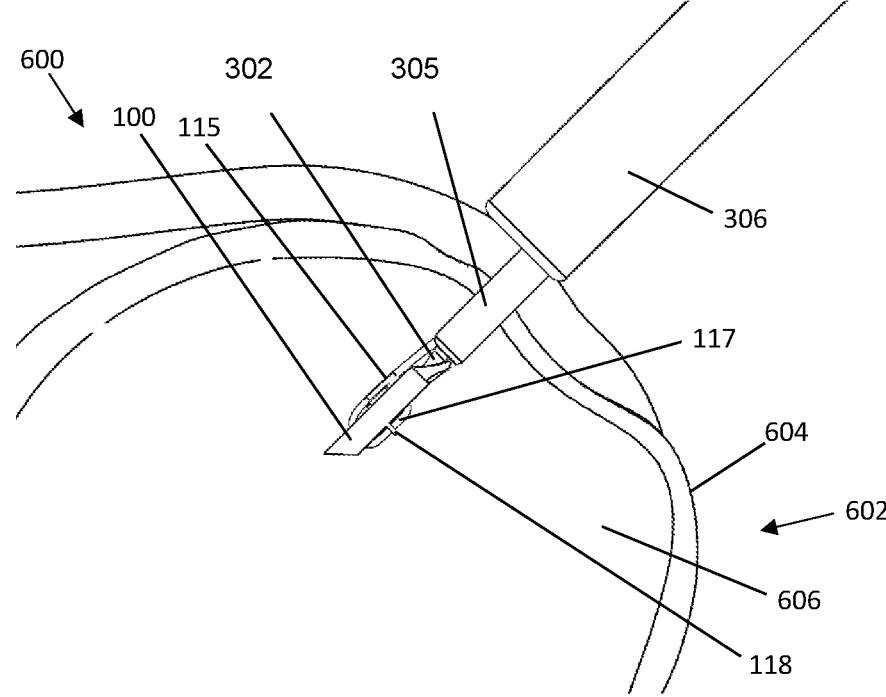
Figure 6D:
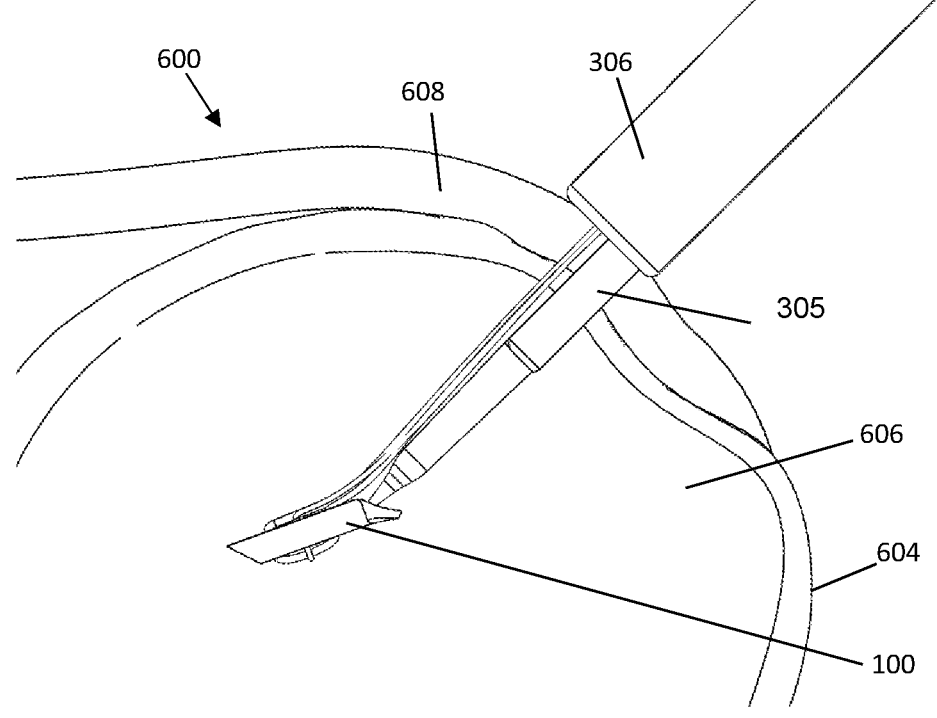

The first toggle type anchor is transferred or inserted into the proximal portion of the anchor delivery tube 306. As shown in FIG. 6C, the bone punch 302 is then reinserted into the lumen of the anchor delivery tube 304 and advanced distally. As shown in FIG. 6D, the toggle body 100 of the anchor is pushed out the distal end by the bone punch 302. The bone punch 302 continues to be advanced in the distal direction to its original depth to push the toggle body 100 into the bone. It has been found that pushing the proximal end of the anchor deep into the bone with the toggle body 100 having an angled distal end causes or at least initiates rotation of the toggle body 100. This initial rotation assures continued rotation upon pulling tension on the working suture 115 outside the body.

Figure 6E:
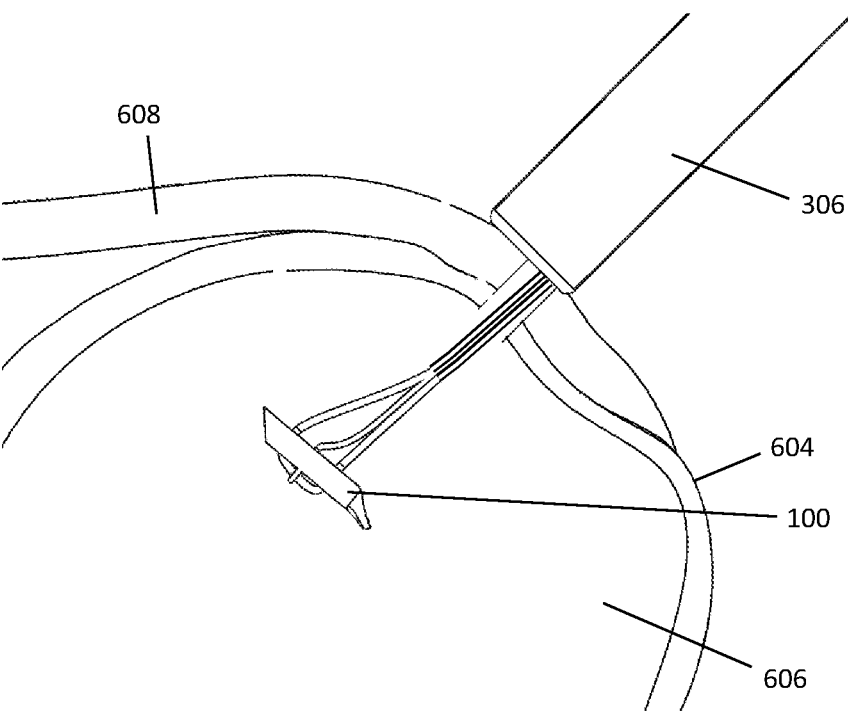
Figure 6F:
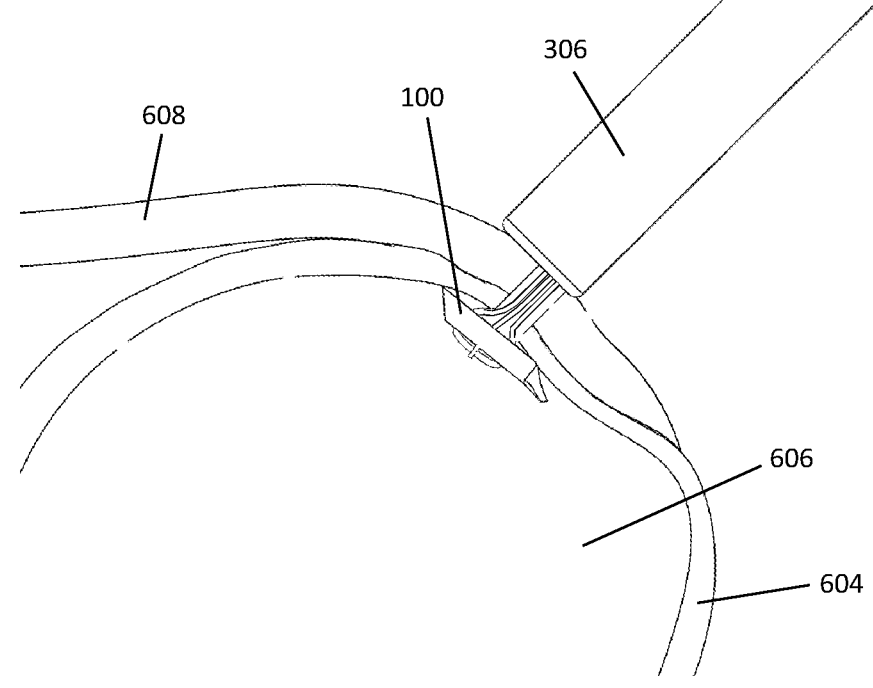
Figure 6G:
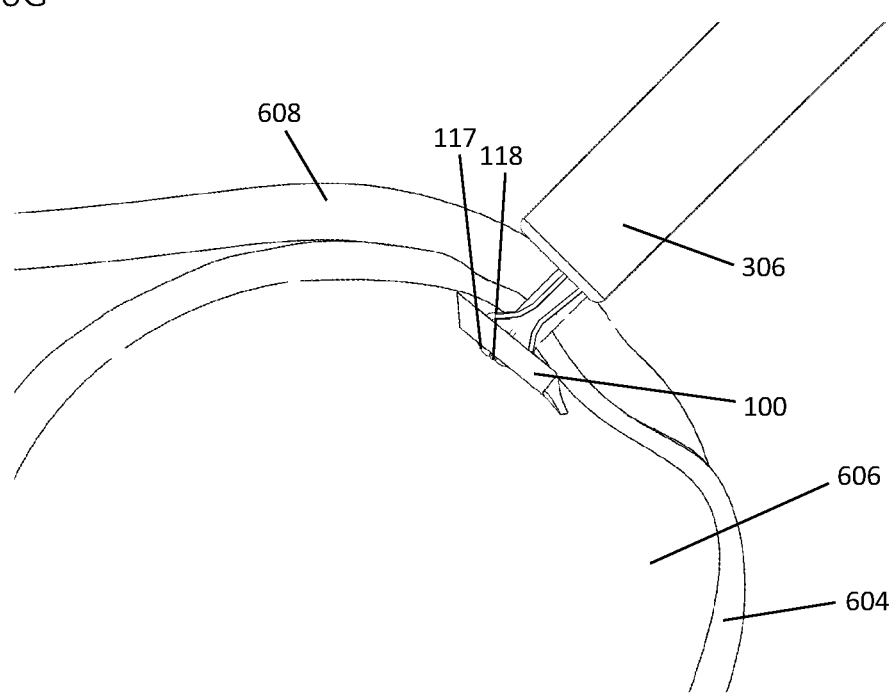
Figure 6H:
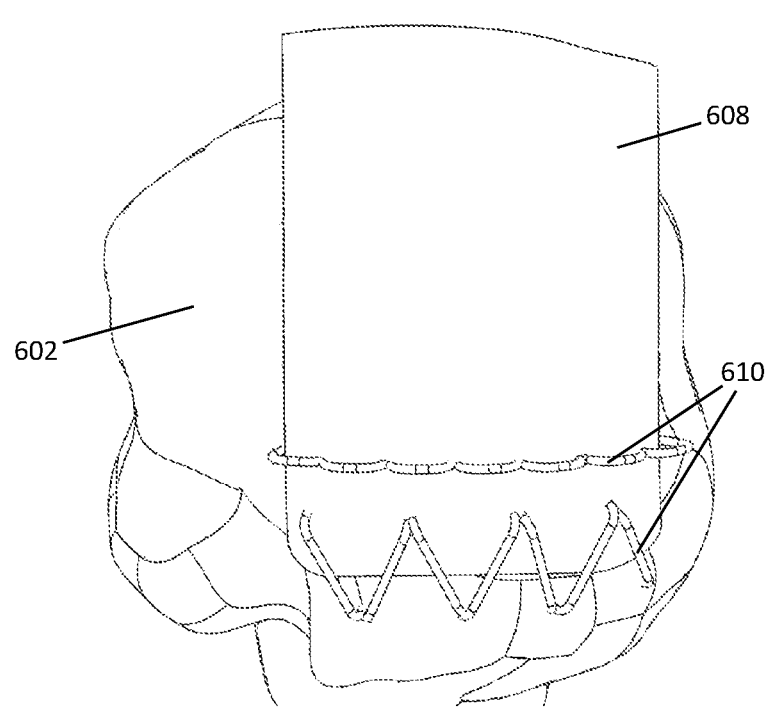
Figure 6I:
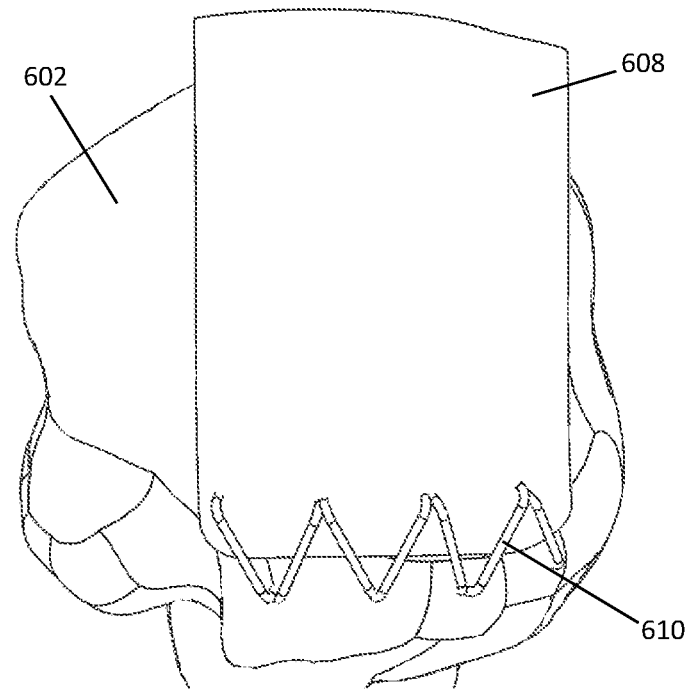

As shown in FIG. 6E, the bone punch 302 and nub 305 are then retracted. This assures the nub 305 does not cut or fray the suture. The nub 305 may be released and allowed to retract under spring force, allowed to stay in place, or positively retracted, as desired. The distal portion of the working suture extending from the distal passage is then pulled to complete the toggling of the anchor as aided by the proximal fins on the toggle body. This is shown in FIG. 6E. With continued tension on the working suture, the anchor 100 is pulled toward the undersurface of the cortical shell of the bone as shown in FIG. 6F. To prevent pullout and/or to support the cortical shell against fracture, counterforce may be applied by pressing the distal end of the anchor delivery tube against the tendon during toggling. As depicted in FIG. 6G, once the working suture 115 is tensioned, the locking suture is tensioned to close the locking loop 118 around the working suture 115 and fix or secure the working suture 115 relative to the toggle body 100. As noted above, in some examples, the locking suture can be broken at a preferential point of weakness or cut, as desired, after the working suture 115 is secured.

With implantation of the first anchor, the working suture 115 is simply locked as it cannot be tensioned to form a stitch until the second anchor is implanted. In some examples, the first anchor in a chain of anchors can be pre-locked for this purpose; in other examples the surgeon will lock the first anchor suture lock at the time of implantation. Therefore, in preferred methods, the second anchor is implanted repeating the above steps, except to the extent that the suture lock is differently engaged. More particularly, as the working suture is pulled to toggle the anchor, the extra suture between the first and second anchors is pulled through to form the tensioned stitch. During suture tensioning the distal end of the elongate tube 306 can be maintained against the outer surface of the tendon to prevent pullout or possible bone fracture at the cortical shell. Once properly tensioned the second anchor is locked. These steps are repeated for the rest of the anchors in an array.

As shown in FIGS. 6H and 6I, using the above method and device can create a row of continuous stitches that closely spaced, individually tensioned and tightened. A preferred pattern includes a row of stitches generally perpendicular to the direction of the tendon force as shown in FIG. 6H. In a rotator cuff repair these would be placed in the medial portion of the original tendon footprint. In some preferred embodiments a second row of anchors is also implanted, especially in a rotator cuff repair. The second row is implanted lateral to the first row and can include a zig zag pattern to put some anchors in the lateral portion of the original footprint and other lateral of the footprint to hold down edges of the repaired tendon. Other configurations are also possible depending on the size and shape of the tear. For example, on a small tear a single zig zag row of stitches could be used as shown in FIG. 6I.

Additional features and alternative designs for various components, subassemblies and assemblies may be found in the following patent applications, each of which is incorporated herein by reference:

U.S. Prov. Pat. App. No. 63/172,564, filed Apr. 8, 2021, titled KNOTLESS MICRO SUTURE ANCHORS AND ANCHOR ARRAYS FOR ANATOMICAL ATTACHMENT OF SOFT TISSUE TO BONE, and U.S. patent application Ser. No. 17/551,588, filed on Dec. 15, 2021 and titled KNOTLESS MICRO SUTURE ANCHORS AND ANCHOR ARRAYS FOR ANATOMICAL ATTACHMENT OF SOFT TISSUE TO BONE.

U.S. Prov. Pat. App. No. 63/172,613, filed Apr. 8, 2021, titled KNOTLESS MICRO SUTURE ANCHOR ARRAY FOR HIGH DENSITY ANATOMICAL ATTACHMENT OF SOFT TISSUE TO BONE, and U.S. patent application Ser. No. 17/551,728, filed on Dec. 15, 2021 and titled KNOTLESS MICRO SUTURE ANCHOR ARRAY FOR HIGH DENSITY ANATOMICAL ATTACHMENT OF SOFT TISSUE TO BONE.

U.S. Prov. Pat. App. No. 63/172,614, filed Apr. 8, 2021, titled METHOD FOR CREATING A TENSIONABLE AND LOCKABLE SUTURE ANCHOR ARRAY FOR ANATOMICAL ATTACHMENT OF SOFT TISSUE TO BONE, and U.S. patent application Ser. No. 17/551,779, filed on Dec. 15, 2021 and titled METHOD FOR CREATING A TENSIONABLE AND LOCKABLE SUTURE ANCHOR ARRAY FOR ANATOMICAL ATTACHMENT OF SOFT TISSUE TO BONE.

U.S. Prov. Pat. App. No. 63/172,629, filed Apr. 8, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE.

U.S. Prov. Pat. App. No. 63/172,624, filed Apr. 8, 2021, titled CARTRIDGE DEVICE FOR SUTURE ANCHOR AND SUTURE MANAGEMENT DURING IMPLANTATION OF A MICRO SUTURE ANCHOR ARRAY, and U.S. patent application Ser. No. 17/551,838, filed on Dec. 15, 2021 and titled CARTRIDGE DEVICE FOR SUTURE ANCHOR AND SUTURE MANAGEMENT DURING IMPLANTATION OF A MICRO SUTURE ANCHOR ARRAY.

U.S. Prov. Pat. App. No. 63/172,568, filed Apr. 8, 2021, titled LOCKING SUTURE CONSTRUCT FOR TENSIONED SUTURE TO SUTURE BRIDGES IN ANCHOR ARRAYS FOR ATTACHING SOFT TISSUE TO BONE and U.S. patent application Ser. No. 17/551,860, filed on Dec. 15, 2021 and titled LOCKING SUTURE CONSTRUCT FOR TENSIONED SUTURE TO SUTURE STITCHES IN ANCHOR ARRAYS FOR ATTACHING SOFT TISSUE TO BONE.

U.S. Prov. Pat. App. No. 63/172,630, filed Apr. 8, 2021, titled METHODS FOR TRANSTENDINOUS IMPLANTATION OF KNOTLESS MICRO SUTURE ANCHORS AND ANCHOR ARRAYS, and U.S. patent application Ser. No. 17/551,885, filed on Dec. 15, 2021 and titled METHODS FOR TRANSTENDINOUS IMPLANTATION OF KNOTLESS MICRO SUTURE ANCHORS AND ANCHOR ARRAYS.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The above description is intended to be illustrative, and not restrictive. For example, the above-described examples (or one or more aspects thereof) may be used in combination with each other. Other embodiments can be used, such as by one of ordinary skill in the art upon reviewing the above description.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A pre-strung array of toggle-type suture anchors comprising:
a plurality of elongated toggle bodies, each having at least a first hole through the toggle body extending from a first longitudinal surface to a second longitudinal surface;
a single suture serially disposed through each of the plurality of toggle bodies, wherein for each toggle body, the suture passing into the first hole at the first longitudinal surface and out the first hole at the second longitudinal surface, wherein the suture is adapted to slide through the first hole of each of the plurality of toggle bodies when a force is applied thereto; and
a separate locking loop for each of the plurality of toggle bodies, each locking loop formed from a separate cord having a free distal end and a free proximal end, the separate cord encircling the suture proximate the second longitudinal surface adjacent one of the elongated toggle bodies, the free distal end of each locking loop forming a slidable knot being adjustable between a first position allowing the suture to slide through the locking loop and a second position that closes the locking loop onto the suture, thereby preventing sliding within the locking loop and preventing sliding of the suture through the first hole in one direction, each locking loop having a point of weakness configured to break and allow removal of the free proximal end of the separate cord.

2. The pre-strung array of toggle-type suture anchors of claim 1, further comprising a second hole through each of the plurality of elongated toggle bodies extending from the first longitudinal surface to the second longitudinal surface at a spaced interval along the elongated toggle body relative to the first hole, wherein for each of the plurality of toggle bodies, the suture exiting the first hole at the second longitudinal surface extends into the second hole on the second longitudinal surface and exits the second hole at the first longitudinal surface with a length of suture extending adjacent the toggle body between the first hole and the second hole near the second longitudinal surface with the locking loop encircling this length of suture.

3. The pre-strung array of toggle-type suture anchors of claim 2, further comprising a third hole through each of the plurality of toggle bodies extending from the first longitudinal surface to the second longitudinal surface and located between the first and second holes, wherein each locking loop extends from the third hole at the second longitudinal surface after passing through the toggle body.

4. The pre-strung array of toggle-type suture anchors of claim 3, wherein the free proximal end of the separate cord extends through the third hole and beyond the first longitudinal surface, to allow collapsing of the locking loop from the first position to the second position when the free proximal end is tensioned.

5. The pre-strung array of toggle-type suture anchors of claim 1, further comprising a second hole through each of the plurality of elongated toggle bodies extending from the first longitudinal surface to the second longitudinal surface at a spaced interval along the elongated toggle body relative to the first hole wherein the suture exiting the first hole at the second longitudinal surface wraps around the elongated toggle body over the top of the suture extending from the first hole, first longitudinal surface then into the second hole through the first longitudinal surface and out the second longitudinal surface to form a one-way locking knot preventing the suture from sliding in one direction but allowing sliding in the other direction.

6. The pre-strung array of toggle-type suture anchors of claim 5, wherein the locking loop encircles at least one of the overlapping sutures proximate their intersection.

7. The pre-strung array of toggle-type suture anchors of claim 6, wherein the locking loop encircles both of the overlapping sutures proximate their intersection.

8. The pre-strung array of toggle-type suture anchors of claim 1, wherein each locking loop compresses the suture adjacent the second longitudinal surface of one of the plurality of elongated toggle bodies when in the second position to thereby prevent the suture sliding through the locking loop.

9. A pre-strung array of toggle-type suture anchors comprising:
a plurality of elongated toggle bodies, each having at least a first hole through the toggle body extending from a first longitudinal surface to a second longitudinal surface;
a single suture serially disposed through each of the plurality of toggle bodies, wherein for each toggle body, the suture passing into the first hole at the first longitudinal surface and out the first hole at the second longitudinal surface, wherein the suture is adapted to slide through the first hole of each of the plurality of toggle bodies when a force is applied thereto; and
a separate locking member for each of the plurality of toggle bodies, each locking member being separate from the suture, each locking member having a free distal end and a free proximal end, each locking member at least partially encircling the suture proximate the second longitudinal surface adjacent one of the plurality of elongated toggle bodies, the free distal end of each locking member forming a slidable knot which is moveable between a first position allowing the suture to slide through the locking member and a second position collapsing the locking member onto the suture and thereby preventing the suture from sliding through the locking member in at least one direction, each locking member having a point of weakness configured to break and allow removal of the free proximal end of the locking member.

10. The pre-strung array of toggle-type suture anchors of claim 8, wherein each locking member is slidably received in a chamber formed in one of the elongated toggle bodies and in the first position has a portion spaced radially from the longitudinal surface to allow suture movement while in the second position locking member is locked deeper within the chamber and creates a pinched tortuous pathway for the suture to prevent suture movement.

11. The pre-strung array of toggle-type suture anchors of claim 9, further comprising a second hole through each of the plurality of elongated toggle bodies extending from the first longitudinal surface to the second longitudinal surface at a spaced interval along the elongated toggle body relative to the first hole, wherein for each of the plurality of toggle bodies, the suture exiting the first hole at the second longitudinal surface extends into the second hole on the second longitudinal surface and exits the second hole at the first longitudinal surface with a length of suture extending adjacent the toggle body between the first hole and the second hole near the second longitudinal surface, the length of suture being encircled by the locking member near the second longitudinal surface.

12. The pre-strung array of toggle-type suture anchors of claim 11, wherein each locking member is slidably disposed in a chamber formed into the elongated body wherein it is movable between the first and second position.

13. The pre-strung array of toggle-type suture anchors of claim 12, wherein in the first position each locking member is positioned adjacent one of the elongated bodies' longitudinal surface to allow suture movement and in the second position pulls the locking member into the chamber sufficient to create a pinched or tortuous path that prevents movement of the suture in at least one direction.

14. The pre-strung array of toggle-type suture anchors of claim 11, further comprising a third hole through each of the plurality of toggle bodies extending from the first longitudinal surface to the second longitudinal surface and located between the first and second holes, wherein each locking member further comprises a pull suture extending from the locking member through the third hole at the first longitudinal surface after passing through the toggle body.

15. The pre-strung array of toggle-type suture anchors of claim 9, wherein each locking member compresses the suture adjacent the second longitudinal surface of one of the plurality of elongated toggle bodies when in the second position to thereby prevent the suture sliding through the locking member.

16. A pre-strung array of toggle-type suture anchors comprising:
   a plurality of elongated toggle bodies, each having at least a first hole through the toggle body extending from a first longitudinal surface to a second longitudinal surface;
   a single suture serially disposed through each of the plurality of toggle bodies, wherein for each toggle body, the suture passing into the first hole at the first longitudinal surface and out the first hole at the second longitudinal surface, wherein the suture is adapted to slide through the first hole of each of the plurality of toggle bodies when a force is applied thereto; and
   a separate suture lock for each of the plurality of toggle bodies, each suture lock adjacent a portion of the suture, each suture lock formed from a separate cord having a free distal end and a free proximal end, the separate cord encircling the suture and having a slidable knot formed from the free distal end and moveable from a first position allowing sliding movement of the suture relative to the toggle body and the suture lock, to a second position that closes the suture lock onto the suture to thereby prevent movement of the suture relative to the toggle body and the suture lock in at least one direction, the suture lock having a point of weakness configured to break and allow removal of the free proximal end of the suture lock.

17. The pre-strung array of toggle-type suture anchors of claim 16, wherein each of the plurality of elongate toggle bodies comprises a generally flat top and bottom surfaces and rounded side surfaces, the rounded side surfaces defining a maximum diameter of the elongate body and each of a proximal, a middle and a distal passage extending from the top surface to the bottom surface, each passage located at spaced intervals along the elongate body with the middle passage between the proximal and distal passages with the suture passing into the proximal passage at the top surface and out at the bottom surface, then back up through the distal passage at the bottom surface out at the top surface leaving a length of suture extending past the middle passage along the bottom surface wherein the cord has a tightening leg extending through the middle passage at the bottom surface and the suture lock encircles a portion of the length of the suture extending past the middle passage along the bottom surface.

18. The pre-strung array of toggle-type suture anchors of claim 17, wherein each suture lock is configured to collapse onto the suture when the tightening leg through the middle passage is tensioned.

19. The pre-strung array of toggle-type suture anchors of claim 18, wherein the middle passage has an upper portion for receiving the slidable knot at least partially therein from the top surface that terminates in a platform within the middle passage that does not allow passage of the slidable knot.

20. The pre-strung array of toggle-type suture anchors of claim 16, wherein each suture lock compresses the suture adjacent the second longitudinal surface of one of the plurality of elongated toggle bodies when in the second position to thereby prevent the suture sliding through the suture lock.

* * * * *